US012434027B2

(12) United States Patent
Zachar et al.

(10) Patent No.: US 12,434,027 B2
(45) Date of Patent: Oct. 7, 2025

(54) MECHANICAL USER CONTROL ELEMENTS FOR FLUID INPUT MODULE

(71) Applicant: AIRWAY MEDIX S.A., Warsaw (PL)

(72) Inventors: Oron Zachar, Tel Aviv (IL); Yair Ramot, Kfar Maas (IL); Eizik Amar, Ashdod (IL)

(73) Assignee: AIRWAY MEDIX S.A., Warsaw (PL)

( * ) Notice: Subject to any disclaimer, the term of this patent is extended or adjusted under 35 U.S.C. 154(b) by 230 days.

(21) Appl. No.: 17/983,657

(22) Filed: Nov. 9, 2022

(65) Prior Publication Data

US 2023/0321379 A1 Oct. 12, 2023

Related U.S. Application Data

(63) Continuation of application No. 16/628,999, filed as application No. PCT/IB2018/054929 on Jul. 3, 2018, now abandoned.

(Continued)

(51) Int. Cl.
*A61M 16/00* (2006.01)
*A61M 16/04* (2006.01)

(52) U.S. Cl.
CPC .... *A61M 16/0463* (2013.01); *A61M 16/0003* (2014.02); *A61M 2205/3334* (2013.01); *A61M 2209/10* (2013.01)

(58) Field of Classification Search
CPC .......... A61M 16/0463; A61M 16/0003; A61M 2205/3334; A61M 2209/10
See application file for complete search history.

(56) References Cited

U.S. PATENT DOCUMENTS

2014/0142496 A1* 5/2014 Zachar .................... A61M 1/76 604/118
2015/0246165 A1 9/2015 Kang
(Continued)

FOREIGN PATENT DOCUMENTS

EP 2809382 B1 3/2017
WO 2017118970 A 7/2017

OTHER PUBLICATIONS

International Search Report from PCT/1B2018/054929; dated Sep. 6, 2018.

*Primary Examiner* — Margaret M Luarca
*Assistant Examiner* — Sarah B Lederer
(74) *Attorney, Agent, or Firm* — FisherBroyles, LLP; Ronni S. Jillions

(57) ABSTRACT

A multi-lumen catheter for cleaning an inner surface of a tracheal ventilation tube is provided, which enables single-handed simultaneous activation of inflation of an inflatable element and suctioning in a closed suction system for use with the tracheal ventilation tube. The closed suction system allows catheters to be used repeatedly without being detached from the tube system including the ventilation air supply. The cleaning catheter is insertable into the tracheal ventilation tube, and is shaped so as to define one or more distal suction orifices. The cleaning catheter comprises an elongate, flexible, tubular catheter main body, and an inflatable element, which is mounted to the catheter main body. An input module is coupled to the cleaning catheter, and comprises an inflation module, which comprises an inflation chamber separate from a suction source. The input module also comprises a flow regulator, which is shaped so as to define a suction port coupleable in fluid communication with the suction source.

21 Claims, 15 Drawing Sheets

Related U.S. Application Data

(60) Provisional application No. 62/528,673, filed on Jul. 5, 2017.

(56) References Cited

U.S. PATENT DOCUMENTS

| | | | | |
|---|---|---|---|---|
| 2015/0343182 | A1* | 12/2015 | Vazales ............. | A61M 16/0463 604/267 |
| 2017/0326317 | A1 | 11/2017 | Zachar | |

* cited by examiner

MECHANICAL USER CONTROL ELEMENTS FOR FLUID INPUT MODULE

CROSS-REFERENCE TO RELATED APPLICATION

PCT/IB2018/054929 filed on Jul. 3, 2018, is incorporated by reference in its entirety. WO 2019/008518 is incorporated by reference in its entirety. PCT/IB2018/054929 claims priority to U.S. provisional patent application No. 62/528,673, filed Jul. 5, 2017, the disclosure of which is incorporated by reference in its entirety'.

FIELD OF THE APPLICATION

The present invention relates generally to medical suction catheter devices, and specifically to catheter devices for aspiration of tracheobronchial secretions and/or cleaning of tracheal ventilation tubes.

BACKGROUND OF THE APPLICATION

Suction catheters are commonly used to aspirate tracheobronchial fluids in patients ventilated with endotracheal tube (ETT) and tracheostomy tube devices. A problematic aspect of the use of suction catheters is the presence of bacterial biofilm within the ETT lumen through winch the suction catheter passes. Consequently, as the suction catheter is inserted, there is high risk of it carrying bacterial biofilm from, the ETT lumen deeper into the bronchial tree where the suction catheter reaches, and thereby increasing the risk of lung infection. Moreover, buildup of substantial biofilm thickness reduces the effective free lumen of the ETT for air passage. Therefore, there is a need for maintaining cleaner ETT lumens between suction operations, and preventing buildup of significant biofilm thickness, UK Publication GB 2482618 A to Einav et al., which is assigned to the assignee of the present application and is incorporated herein by reference, describes a multi-lumen catheter for multiple fluids conduction, including balloon inflation with air via an inflation lumen, suction via a suction lumen, and cleaning fluids delivery via a cleaning fluid-delivery lumen.

U.S. Pat. No. 8,999,074 to Zachar et al., which is assigned to the assignee of the present application and is incorporated herein by reference, describes a cleaning catheter that includes fluid-delivery' and suction lumens. A flow regulator defines suction and fluid ports. A mechanical user control element is configured to mechanically and non-electrically set activation states of the flow regulator, and transition between first and third configurations via a second configuration. When the control element is in the first configuration, the flow regulator blocks fluid communication (a) between the suction port and the suction lumen and (b) between the fluid port and the fluid-delivery lumen. When the control element is in the second configuration, the flow regulator effects fluid communication between the suction port and the suction lumen, and blocks fluid communication between the fluid port and the fluid-delivery lumen. When the control element is in the third configuration, the flow regulator effects fluid communication (a) between the suction port and the suction-orifice lumen and (b) between the fluid port and the fluid-delivery lumen.

SUMMARY OF THE APPLICATION

Some applications of the present invention provide a multi-lumen catheter for cleaning an inner surface of a tracheal ventilation tube. Some techniques of the present invention enable single-handed simultaneous activation of inflation of an inflatable element and suctioning in a closed suction system for use with the tracheal ventilation tube. A closed suction system allows catheters to be used repeatedly without being detached from the tube system including the ventilation air supply.

The cleaning catheter is insertable into the tracheal ventilation tube, and is shaped so as to define one or more distal suction orifices. The cleaning catheter comprises an elongate, flexible, tubular catheter main body, and an inflatable element, which is mounted to the catheter main body. An input module is coupled to the cleaning catheter, and comprises an inflation module, which comprises an inflation chamber separate from a suction source. The input module also comprises a flow regulator, which is shaped so as to define a suction port coupleable in fluid communication with the suction source.

The input module further comprises a plurality of mechanical user-control buttons. The buttons typically include a mechanical inflation-chamber-control button, which is configured to (a) assume (i) at least a first spatial position when not depressed, and (ii) a second spatial position when fully depressed, and (b) mechanically and non-electrically cause an increase in pressure in an interior of the inflation chamber during a transition of the mechanical inflation-chamber-control button from its first spatial position toward its second spatial position. Typically, the plurality of mechanical user-control buttons further include one or more non-inflation-chamber-control buttons, which are not configured upon depression thereof to cause the increase in pressure in the interior of the inflation chamber.

For some applications, the one or more non-inflation-chamber-control buttons comprise a mechanical suction-control button, which is configured to assume (a) at least a first spatial position when not depressed and (b) a second spatial position when fully depressed. For some applications, the input module is arranged such that:

- when the mechanical suction-control button is in its first spatial position, the flow regulator (a) blocks fluid communication between the suction source and the one or more distal suction orifices, and (b) enables fluid communication between the suction source and the interior of the inflatable element via an inflatable-element lumen, thereby deflating and/or maintaining deflation of the inflatable element, and
- when the mechanical suction-control button is in its second spatial position, the flow regulator blocks fluid communication between the suction source and the interior of the inflatable element.

For some applications, the input module is arranged such that, if suction having a strength of 25 cm H2O and a flow rate of 4 cc/second is applied to the suction port:

- a pressure within the inflatable element is less than 25 cm H2O at two seconds ager completion of depressing, and while maintaining, the mechanical inflation-chamber-control button as far as possible (without breaking any elements) toward its second spatial position without depression of any of the other mechanical user-control buttons of the input module.

For practical purposes, the inflatable element is herein considered functionally deflated when its internal pressure is at a pressure of less than 25 cm H2O, and fully deflated when at negative pressure. This arrangement of the input module prevents accidental substantial inflation of the inflatable element without also applying suction to the distal suction orifices. Such inflation without suction is not desirable because if the balloon were inflated and accidentally withdrawn along the ventilation tube without also applying suction to the distal suction orifices, the biofilm wiped by the inflatable element from the inner surface of the ventilation tube would accumulate and be dragged up toward the ventilation connection rather than be removed from the ventilation circuit. This arrangement prevents such undesired inflation without the necessity of locking any of the mechanical user-control buttons, including the mechanical inflation-chamber-control button.

There is therefore provided, in accordance with an application of the present invention, apparatus for use with a tracheal ventilation tube and a suction source, the apparatus including:

(A) a cleaning catheter, which is insertable into the ventilation tube and includes:
  (i) an elongate, flexible, tubular catheter main body, which is shaped so as to define (a) one or more distal suction orifices, (b) a suction-orifice lumen, and (c) an inflatable-element lumen, and
  (ii) an inflatable element, which is mounted to the catheter main body, and which is shaped so as to define an interior that is in fluid communication with the inflatable-element lumen; and
(B) an input module, which is coupled to the cleaning catheter, and includes:
  (i) an inflation module, which includes an inflation chamber separate from the suction source;
  (ii) a flow regulator, which is shaped so as to define a suction port coupleable in fluid communication with the suction source; and
  (iii) a plurality of mechanical user-control buttons, which include:
    (1) a mechanical inflation-chamber-control button, which is configured to (a) assume at least a first spatial position when not depressed, and a second spatial position when fully depressed, and (b) mechanically and non-electrically cause an increase in pressure in an interior of the inflation chamber during a transition of the mechanical inflation-chamber-control button from its first spatial position toward its second spatial position; and
    (2) one or more non-inflation-chamber-control buttons, which are not configured upon depression thereof to cause the increase in pressure in the interior of the inflation chamber, wherein the input module is arranged such that, if suction having a strength of 25 cm H2O and a flow rate of 4 cc/second is applied to the suction port:

a pressure within the inflatable element is less than 25 cm H2O at two seconds after completing, and while maintaining, depression of the mechanical inflation-chamber-control button as far as possible toward its second spatial position and without depression of any of the other mechanical user-control buttons of the input module.

For some applications, a volume of the inflation chamber when the mechanical inflation-chamber-control button is in its first spatial position is at least 25% greater than a volume of the interior of the inflatable element when the pressure within the inflatable element equals 25 cm H2O.

For some applications, the inflatable element is mounted to the catheter main body at a location within 3 cm of at least one of the one or more distal suction orifices.

For some applications, the suction port is coupled in fluid communication with suction source.

For some applications, the inflation chamber has a volume of between 1 and 10 cc when the first mechanical control element is in its first spatial position.

For some applications, the mechanical suction-control button and the mechanical inflation-chamber-control button are biased toward their respective first spatial positions.

For some applications, the input module includes one or more springs that are arranged to bias the mechanical suction-control button and the mechanical inflation-chamber-control button toward their respective first spatial positions.

For some applications, the input module includes exactly one spring that is arranged to bias both the mechanical suction-control button and the mechanical inflation-chamber-control button toward their respective first spatial positions.

For some applications, the inflation chamber includes an elastic compartment, and the input module is configured such that the transition of the mechanical inflation-chamber-control button from its first spatial position to its second spatial position compresses the elastic compartment, thereby mechanically and non-electrically causing the increase in the pressure in an interior of the elastic compartment.

For any of the applications described above, the input module may be arranged such that upon depression of the mechanical inflation-chamber-control button as far as possible toward its second spatial position and without depression of any of the other mechanical user-control buttons of the input module, the flow regulator does not connect the interior of the inflation chamber in fluid communication with the interior of the inflatable element.

For any of the applications described above, the input module may be arranged such that when the mechanical inflation-chamber-control button is depressed as far as possible toward its second spatial position and without depression of any of the other mechanical user-control buttons of the input module, the flow regulator (a) enables fluid communication between the interior of the inflation chamber and the interior of the inflatable element via the inflatable-element lumen, and (b) enables fluid communication between the suction source and the interior of the inflatable element via the inflatable-element lumen.

For any of the applications described above:

the one or more non-inflation-chamber-control buttons may include a mechanical suction-control button, which is configured to assume at least a first spatial position when not depressed, and a second spatial position when fully depressed, and the input module may be arranged such that:
  when the mechanical suction-control button is in its first spatial position, the flow regulator (a) blocks fluid communication between the suction source and the one or more distal suction orifices, and (b) enables fluid communication between the suction source and the interior of the inflatable element via the inflatable-element lumen, and
  when the mechanical suction-control button is in its second spatial position, the flow regulator blocks fluid communication between the suction source and the interior of the inflatable element.

For some applications, the input module is arranged such that upon depression of the mechanical inflation-chamber-control button as far as possible toward its second spatial position and without depression of the mechanical suction-control button, the flow regulator does not connect the interior of the inflation chamber in fluid communication with the interior of the inflatable element.

For some applications, the input module is arranged such that when the mechanical inflation-chamber-control button is depressed as far as possible toward its second spatial position without depression of the mechanical suction-control button, the flow regulator (a) enables fluid communication between the interior of the inflation chamber and the interior of the inflatable element via the inflatable-element lumen, and (b) enables fluid communication between the suction source and the interior of the inflatable element via the inflatable-element lumen.

For some applications, the mechanical suction-control and inflation-chamber-control buttons are positioned on the input module such that when the mechanical suction-control and inflation-chamber-control buttons are in their respective first spatial positions, the mechanical suction-control and inflation-chamber-control buttons can be depressed and transitioned to their respective second spatial positions by application of a force to the mechanical suction-control and inflation-chamber-control buttons by a single 1 cm-by-2 cm rectangular surface.

For some applications, the input module is arranged such that depression of one of the mechanical suction-control and inflation-chamber-control buttons does not automatically cause depression, by the input module, of the other of the mechanical suction-control and inflation-chamber-control buttons.

For some applications, the input module is arranged such that depression of the mechanical suction-control button does not cause an increase in pressure in the interior of the inflation chamber during a transition of the mechanical suction-control button from its first spatial position toward its second spatial position.

For some applications, the input module is arranged such that depression of the mechanical inflation-chamber-control button does not cause connection of the suction source in fluid communication with the one or more distal suction orifices via the suction-orifice lumen during a transition of the mechanical inflation-chamber-control button from its first spatial position toward its second spatial position.

For some applications, the input module is arranged such that during simultaneous depression of the mechanical suction-control and inflation-chamber-control buttons, a resulting simultaneous transition of the mechanical suction-control and inflation-chamber-control buttons from their respective first spatial positions to their respective second spatial positions causes the flow regulator to:

- connect the suction source in fluid communication with the one or more distal suction orifices via the suction-orifice lumen, and
- connect the interior of the inflation chamber in fluid communication with the interior of the inflatable element via the inflatable-element lumen, thereby inflating the inflatable element, while maintaining the suction source in fluid communication with the one or more distal suction orifices via the suction-orifice lumen.

For some applications, the input module is arranged such that during the simultaneous depression of the mechanical suction-control and inflation-chamber-control buttons, the resulting simultaneous transition of the mechanical suction-control and inflation-chamber-control buttons from their respective first spatial positions to their respective second spatial positions causes the flow regulator:

- first, to connect the suction source in fluid communication with the one or more distal suction orifices via the suction-orifice lumen, and
- thereafter, to connect the interior of the inflation chamber in fluid communication with the interior of the inflatable element via the inflatable-element lumen, thereby inflating the inflatable element, while maintaining the suction source in fluid communication with the one or more distal suction orifices via the suction-orifice lumen.

For some applications, the input module is arranged such that during simultaneous depression of the mechanical suction-control and inflation-chamber-control buttons, a resulting simultaneous transition of the mechanical suction-control and inflation-chamber-control buttons from their respective first spatial positions to their respective second spatial positions causes:

- first, the flow regulator to disconnect the suction source from the fluid communication with the interior of the inflatable element, and
- thereafter, the flow regulator to connect the interior of the inflation chamber in fluid communication with the interior of the inflatable element via the inflatable-element lumen, thereby inflating the inflatable element, while maintaining the suction source in fluid communication with the one or more distal suction orifices via the suction-orifice lumen.

For some applications:

- the input module includes a housing, which is shaped so as to define an internal channel,
- the flow regulator includes a proximal input portion of the cleaning catheter, which proximal input portion is disposed within and is axially slidable with respect to the internal channel of the housing of the input module, and
- the input module and the proximal input portion are arranged such that:
  - when the mechanical suction-control and inflation-chamber-control buttons are in their respective first spatial positions, the proximal input portion is at a first axial position with respect to the internal channel of the housing of the input module, in which first axial position the proximal input portion blocks fluid communication between the suction source and the one or more distal suction orifices, and
  - during the simultaneous depression of the mechanical suction-control and inflation-chamber-control buttons:
    - first, the mechanical suction-control button causes the proximal input portion to slide axially with respect to the internal channel from the first axial position to a second axial position, in which second axial position the proximal input portion connects the suction source in fluid communication with the one or more distal suction orifices via the suction-orifice lumen, and
    - thereafter, the mechanical inflation-chamber-control button causes the proximal input portion to slide axially with respect to the internal channel from the second axial position to a third axial position, in which third axial position the proximal input portion connects the interior of the inflation chamber in fluid communication with the interior of the inflatable element.

For some applications:

- the input module includes a housing, which is shaped so as to define an internal channel,
- the flow regulator includes a proximal input portion of the cleaning catheter, which proximal input portion is disposed within and axially slidable with respect to the internal channel of the housing of the input module, the flow regulator includes a pressure-actuated one-way valve, and the input module and the proximal input portion are arranged such that:

when the mechanical suction-control and inflation-chamber-control buttons are in their respective first spatial positions, the proximal input portion is at a first axial position with respect to the internal channel of the housing of the input module, in which first axial position the proximal input portion blocks fluid communication between the suction source and the one or more distal suction orifices, and during the simultaneous depression of the mechanical suction-control and inflation-chamber-control buttons:

first, the mechanical suction-control button causes the proximal input portion to slide axially with respect to the internal channel from the first axial position to a second axial position, in which second axial position the proximal input portion connects the suction source in fluid communication with the one or more distal suction orifices via the suction-orifice lumen, and thereafter, the increase in pressure in the interior of the inflation chamber caused by the transition of the mechanical inflation-chamber-control button from its first spatial position toward its second spatial position causes the pressure-actuated one-way valve to open, thereby connecting the interior of the inflation chamber in fluid communication with the interior of the inflatable element via the inflatable-element lumen.

For some applications, the input module is arranged such that upon depression of the mechanical suction-control button and without depression of the mechanical inflation-chamber-control button, the flow regulator enables fluid communication between the suction source and the one or more distal suction orifices via the suction-orifice lumen, without enabling fluid communication between the interior of the inflation chamber and the interior of the inflatable element.

For some applications, the input module further includes a locking mechanism, which is configured to assume:

an unlocked state, in which the mechanical suction-control button and the mechanical inflation-chamber-control button can be depressed, and a locked state, in which the mechanical suction-control button cannot be depressed, and the mechanical inflation-chamber-control button can be depressed.

For any of the applications described above, the mechanical inflation-chamber-control button may be configured to cause the increase in the pressure in the interior of the inflation chamber by mechanically and non-electrically compressing the inflation chamber during the at least a portion of the transition of the mechanical inflation-chamber-control button from its first spatial position to its second spatial position.

For some applications, the inflation chamber transitions from a lower level of compression to a higher level of compression during the at least a portion of the transition of the mechanical inflation-chamber-control button from its first spatial position to its second spatial position, and the input module is configured to elastically bias the inflation chamber toward the lower level of compression.

For some applications, the inflation module is elastically biased toward the lower level of compression.

There is further provided, in accordance with an application of the present invention, apparatus for use with a tracheal ventilation tube and a suction source, the apparatus including:

(A) a cleaning catheter, which is insertable into the ventilation tube and includes:

(i) an elongate, flexible, tubular catheter main body, which is shaped so as to define (a) one or more distal suction orifices, (b) a suction-orifice lumen, and (c) an inflatable-element lumen; and (ii) an inflatable element, which is mounted to the catheter main body, and which is shaped so as to define an interior that is in fluid communication with the inflatable-element lumen; and (B) an input module, which is coupled to the cleaning catheter, and includes:

(i) an inflation module, which includes an inflation chamber separate from the suction source:

(ii) a flow regulator, which is shaped so as to define a suction port coupleable in fluid communication with the suction source;

(iii) a mechanical suction-control button, which is configured to assume at least a first spatial position when not depressed, and a second spatial position when fully depressed; and (iv) a mechanical inflation-chamber-control button, which is configured to (a) assume at least a first spatial position when not depressed, and a second spatial position when fully depressed, and (b) mechanically and non-electrically cause an increase in pressure in an interior of the inflation chamber during a transition of the mechanical inflation-chamber-control button from its first spatial position toward its second spatial position, wherein the input module is arranged such that:

when the mechanical suction-control button is in its first spatial position, the flow regulator (a) blocks fluid communication between the suction source and the one or more distal suction orifices, and (b) enables fluid communication between the suction source and the interior of the inflatable element via the inflatable-element lumen, and when the mechanical suction-control button is in its second spatial position, the flow regulator blocks fluid communication between the suction source and the interior of the inflatable element, and wherein the input module is arranged such that, if suction having a strength of 25 cm H2O and a flow rate of 4 cc/second is applied to the suction port:

a pressure within the inflatable element is less than 25 cm H2O at two seconds after completing, and while maintaining, depression of the mechanical inflation-chamber-control button as far as possible toward its second spatial position and without depression of mechanical suction-control button.

There is still further provided, in accordance with an application of the present invention, apparatus for use with a tracheal ventilation tube and a suction source, the apparatus including:

(A) a cleaning catheter, which is insertable into the ventilation tube and includes:

(i) an elongate, flexible, tubular catheter main body, which is shaped so as to define (a) one or more distal suction orifices, (b) a suction-orifice lumen, and (c) an inflatable-element lumen; and (ii) an inflatable element, which is mounted to the catheter main body, and which is shaped so as to define an interior that is in fluid communication with the inflatable-element lumen; and (B) an input module, which is coupled to the cleaning catheter, and includes:

(i) an inflation module, which includes an inflation chamber separate from the suction source;

(ii) a flow regulator, which is shaped so as to define a suction port coupleable in fluid communication with the suction source; and (iii) a plurality of mechanical user-control buttons, which include:

(1) a mechanical inflation-chamber-control button, which is configured to (a) assume at least a first spatial position when not depressed, and a second spatial position when fully depressed, and (b) mechanically and non-electrically cause an increase in pressure in an interior of the inflation chamber during a transition of the mechanical inflation-chamber-control button from its first spatial position toward its second spatial position; and (2) one or more non-inflation-chamber-control buttons, which are not configured upon depression thereof to cause the increase in pressure in the interior of the inflation chamber, wherein the input module is arranged such that upon depression of the mechanical inflation-chamber-control button as far as possible toward its second spatial position and without depression of any of the other mechanical user-control buttons of the input module, the flow regulator does not connect the interior of the inflation chamber in fluid communication with the interior of the inflatable element.

There is additionally provided, in accordance with an application of the present invention, apparatus for use with a tracheal ventilation tube and a suction source, the apparatus including:

(A) a cleaning catheter, which is insertable into the ventilation tube and includes:

(i) an elongate, flexible, tubular catheter main body, which is shaped so as to define (a) one or more distal suction orifices, (b) a suction-orifice lumen, and (c) an inflatable-element lumen; and (ii) an inflatable element, which is mounted to the catheter main body, and which is shaped so as to define an interior that is in fluid communication with the inflatable-element lumen; and (B) an input module, which is coupled to the cleaning catheter, and includes:

(i) an inflation module, which includes an inflation chamber separate from the suction source;

(ii) a flow regulator, which is shaped so as to define a suction port coupleable in fluid communication with the suction source; and (iii) a plurality of mechanical user-control buttons, which include:

(1) a mechanical inflation-chamber-control button, which is configured to (a) assume at least a first spatial position when not depressed, and a second spatial position when fully depressed, and (b) mechanically and non-electrically cause an increase in pressure in an interior of the inflation chamber during a transition of the mechanical inflation-chamber-control button from its first spatial position toward its second spatial position; and (2) one or more non-inflation-chamber-control buttons, which are not configured upon depression thereof to cause the increase in pressure in the interior of the inflation chamber, wherein the input module is arranged such that when the mechanical inflation-chamber-control button is depressed as far as possible toward its second spatial position and without depression of any of the other mechanical user-control buttons of the input module, the flow regulator:

enables fluid communication between the interior of the inflation chamber and the interior of the inflatable element via the inflatable-element lumen, and enables fluid communication between the suction source and the interior of the inflatable element via the inflatable-element lumen.

There is yet additionally provided, in accordance with an application of the present invention, a method for use with a tracheal ventilation tube and a suction source, the method including:

coupling, in fluid communication with the suction source, a suction port of a flow regulator of an input module, wherein the input module includes (i) an inflation module, which includes an inflation chamber separate from the suction source, (ii) a plurality of mechanical user-control buttons, which include (1) a mechanical inflation-chamber-control button, which is configured to (a) assume at least a first spatial position when not depressed, and a second spatial position when fully depressed, and (b) mechanically and non-electrically cause an increase in pressure in an interior of the inflation chamber during a transition of the mechanical inflation-chamber-control button from its first spatial position toward its second spatial position, and (2) one or more non-inflation-chamber-control buttons, which are not configured upon depression thereof to cause the increase in pressure in the interior of the inflation chamber; and while the mechanical inflation-chamber-control button is in the first spatial position, inserting a cleaning catheter, in a proximal to distal direction, into the tracheal ventilation tube inserted in a trachea of a patient, and advancing the cleaning catheter until a distal end of the catheter main body is axially disposed in the tracheal ventilation tube at a location more distal than an axial mid-point of the tracheal ventilation tube, wherein the cleaning catheter is coupled to the input module and includes (i) an elongate, flexible, tubular catheter main body, which is shaped so as to define (a) one or more distal suction orifices, (b) a suction-orifice lumen, and (c) an inflatable-element lumen, and (ii) an inflatable element, which is mounted to the catheter main body, and which is shaped so as to define an interior that is in fluid communication with the inflatable-element lumen, wherein the input module is arranged such that, if suction having a strength of 25 cm H2O and a flow rate of 4 cc/second is applied to the suction port:

a pressure within the inflatable element is less than 25 cm H2O at two seconds after completing, and while maintaining, depression of the mechanical inflation-chamber-control button as far as possible toward its second spatial position and without depression of any of the other mechanical user-control buttons of the input module.

The present invention will be more fully understood from the following detailed description of embodiments thereof, taken together with the drawings, in which:

DETAILED DESCRIPTION OF APPLICATIONS

The figures are schematic illustrations of several configurations of a closed suction cleaning system 100, in accordance with respective applications of the present invention. Cleaning system 100 is typically configured for use with a tracheal ventilation tube, a ventilator, and a suction source. For some applications, cleaning system 100 comprises one or more of the tracheal ventilation tube, the ventilator, and/or the suction source, in any combination. Although these elements are not illustrated in the figures, they can be seen in FIGS. 1A-D of U.S. Pat. No. 8,999,074 to Zachar et al., which is incorporated herein by reference. Cleaning system 100 may be implemented as shown in FIGS. 1A-D of the '074 patent, mutatis mutandis, except that cleaning system 100 typically does not comprise the pressurized fluid source 602 shown in these figures.

As used in the present application, including in the claims, a "tracheal ventilation tube" comprises an endotracheal tube (ETT) or a tracheostomy tube. For some applications, the suction source provides a pressure less than one atm; alternatively or additionally, for some applications, the suction source provides a pressure lower than ambient pressure. As used in the present application, including in the claims, a "fluid" comprises liquid and/or gas, for example, a liquid-gas mixture that is predominantly liquid, such as a liquid with gas bubbles. The liquid may comprise water, such as saline solution or a disinfectant solution.

Figure 1:
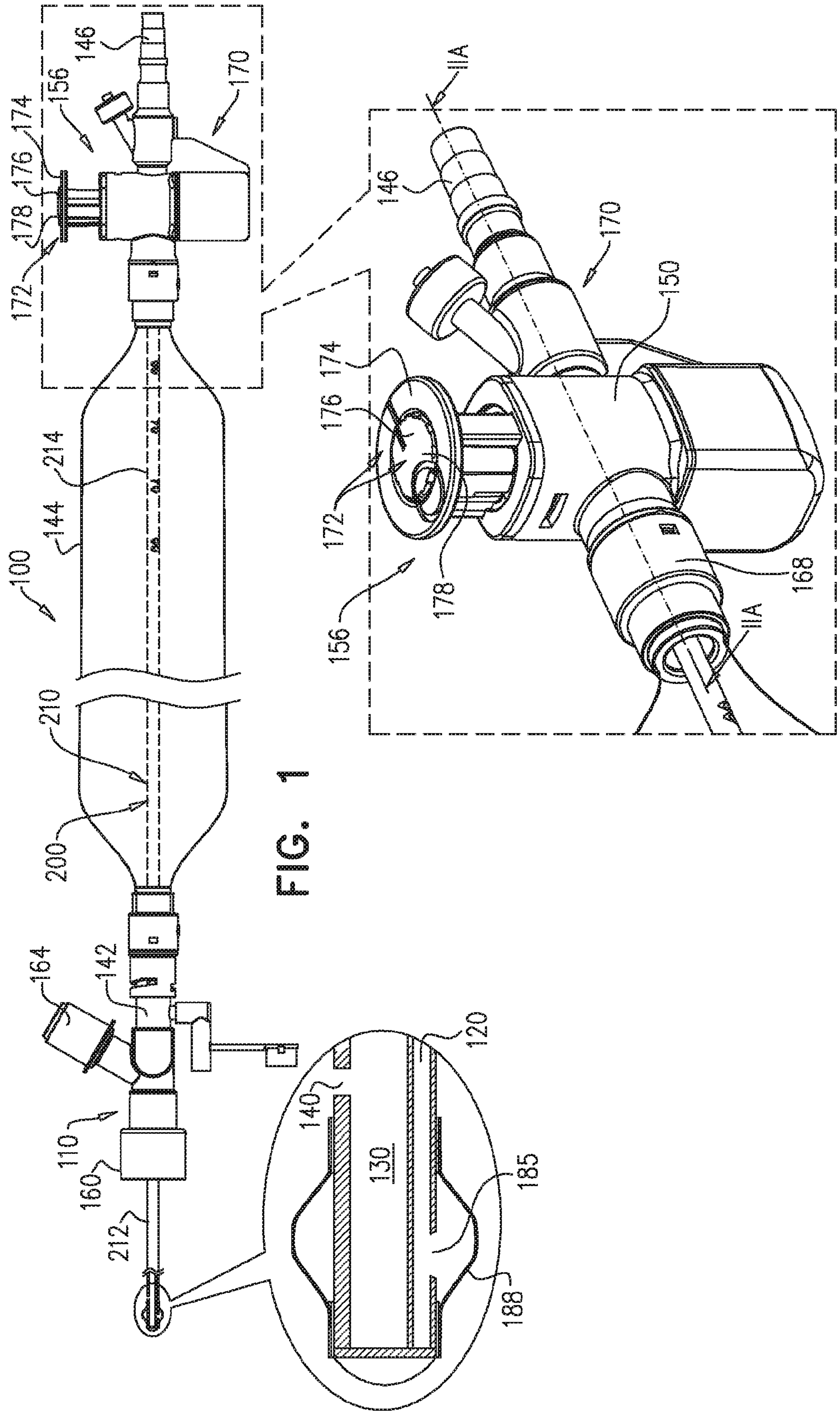
FIG. 1 is a schematic illustration of a closed suction cleaning system, in accordance with an application of the present invention.

Reference is made to FIG. 1, which is a schematic illustration of cleaning system 100, in accordance with an application of the present invention. Cleaning system 100 typically comprises a distal ventilation tube-connector assembly 110, a cleaning catheter 200, and an input module 156. Cleaning catheter 200 comprises an elongate, flexible, tubular catheter main body 210. Cleaning catheter 200 includes a distal portion 212 located distal to ventilation tube-connector assembly 110, and a proximal portion 214 (labeled in the other figures) located proximal to ventilation tube-connector assembly 110. Distal portion 212 is configured to be inserted into the ventilation tube. Proximal portion 214 includes a proximal input portion 216 of catheter main body 210, which is configured to be inserted into or is disposed within input module 156. Typically, proximal input portion 216 is axially slidable with respect to input module 156. Respective lengths of distal and proximal portions 212 and 214 may depend on an extent to which a distal end of catheter main body 210 is deployed within the ventilation tube and/or an extent to which the distal end is longitudinally displaced from ventilation tube-connector assembly 110, for example, an extent to which catheter main body 210 slides through ventilation tube-connector assembly 110 in a distal direction.

As used in the present application, including in the claims, "axial" and "axially" mean along an axis, and do not mean around or about an axis. For example: (a) "axial motion" means motion along an axis, and (b) "axially aligned" means aligned along an axis.

Ventilation tube-connector assembly 110 comprises: (a) a ventilator port 164, configured to be coupled in fluid communication with the ventilator via a ventilator connection tube, (b) a ventilation tube port 160, configured to be coupled in fluid communication with a proximal end of the ventilation tube, and (c) a main body inlet 142, which is configured to allow passage therethrough of catheter main body 210.

In some applications of the present invention, cleaning system 100 is operative to clean an interior of the ventilation tube when ventilation tube-connector assembly 110 is directly or indirectly connected to both the ventilation tube and the ventilator so as to mediate a substantially air-tight connection (e.g., via an interior chamber(s) and/or conduit(s) of ventilation tube-connector assembly 110) between the ventilator and an interior of the ventilation tube.

Cleaning catheter 200 further comprises an inflatable element 188, such as a balloon, which is mounted to catheter main body 210 near a distal end of catheter main body 210, e.g., within 3 cm, such as within 1 cm, of the distal end, and/or in a distal half of distal portion 212 of cleaning catheter 200, such as a distal third, a distal fifth, or a distal tenth of distal portion 212. Alternatively or additionally, inflatable element 188 is mounted to catheter main body 210 within 3 cm, e.g., within 1 cm, of at least one of the one or more distal suction orifices 140, described hereinbelow. Inflatable element 188 is inflatable into contact with an inner surface of the ventilation tube. For some applications, inflatable element 188 has a greatest outer diameter of at least 6 mm, no more than 12 mm, and/or between 6 and 12 mm when inflated at 1 bar above atmospheric pressure and unconstrained (i.e., not constrained by the ventilation tube or anything else), which is typically slightly greater than an inner diameter of the ventilation tube, in order to provide sealing contact with the inner surface of the ventilation tube. For some applications, inflatable element 188 has a volume of at least 0.5 cc, no more than 2 cc, and/or between 0.5 and 2 cc when inflated at 1 bar above atmospheric pressure and unconstrained. For some applications, inflatable element 188 is elastic, while for other applications inflatable element 188 is not elastic. For some applications, inflatable element 188 comprises a thin pliable material, such that the inflammable element crumples when deflated.

For some applications, catheter main body 210 has an outer diameter of at least 6 mm, no more than 12 mm, and/or between 6 and 12 mm. For some applications, the greatest outer diameter of inflatable element 188 when fully inflated and unconstrained (i.e., not constrained by the ventilation tube or anything else) equals at least 60%, no more than 120%, and/or between 60% and 120% of the outer diameter of catheter main body 210.

Reference is still made to FIG. 1 and is additionally made to FIGS. 2A-D, 3A-D, and 4A-D, which are schematic cross-sectional illustrations of respective implementations of input module 156 of closed suction cleaning system 100, in accordance with respective applications of the present invention. In particular, FIGS. 2A-D, 3A-D, and 4A-D are schematic illustrations of closed suction cleaning systems 300, 400, and 500, respectively, which are respective implementations of closed suction cleaning system 100. Closed suction cleaning systems 300, 400, and 500 comprise input modules 356, 456, and 556, respectively, which are respective implementations of input module 156.

Catheter main body 210 typically includes a plurality of lumens arranged along catheter main body 210. For some applications, one or more of the lumens are arranged along catheter main body 210 at least partially within the main body, e.g., integrally formed in the catheter main body 210, formed in the wall of catheter main body 210, or provided as a separate tube with catheter main body 210. Alternatively or additionally, one or more of the lumens are arranged along catheter main body 210 at least partially outside the main body, e.g., provided as a separate tube outside catheter main body 210. The lumens typically include:

- an inflatable-element lumen 120, which provides fluid communication between at least one inflation inlet 121 and at least one inflation port 185 which is in fluid communication with an interior of inflatable element 188; typically, the input portion is shaped so as to define inflation inlet 121, and distal portion 212 is shaped so as to define inflation port 185; and
- a suction-orifice lumen 130, which provides fluid communication between at least one proximal suction inlet 131 and the one or more distal suction orifices 140; typically, the input portion of catheter main body 210 is shaped so as to define proximal suction inlet 131, and distal portion 212 of cleaning catheter 200 is shaped so as to define distal suction orifices 140. The at least one suction-orifice lumen 130 is arranged in intermittent fluid communication with the suction source, as described in detail hereinbelow.

Inflatable-element lumen 120 typically has a cross-sectional area smaller than that of suction-orifice lumen 130, e.g., less than 50%, less than 30%, or less than 20% of the cross-sectional area of suction-orifice lumen 130. For some applications (as shown), proximal input portion 216 of catheter main body 210 can be arbitrarily rotationally oriented within input module 156, because fluid flow access to inflation inlet 121 of inflatable-element lumen 120 is provided around the entire circumference of proximal input portion 216, via a small circumferential gap between the outer surface of proximal input portion 216 and an internal surface of the internal channel of housing 168, which is described hereinbelow.

When inflated, inflatable element 188 typically provides wiping functionality useful for cleaning the inner surface of the ventilation tube. Typically, in order to provide this wiping functionality, inflatable element 188, when inflated, maintains a gas pressure of at least 30 cm H2O (typically substantially higher). Typically, this gas pressure is achieved at least when mechanical suction-control and inflation-chamber-control buttons 178 and 174, described hereinbelow, are depressed continuously for at least five seconds. Optionally, inflatable element 188, when inflated, additionally provides flow obstruction functionality to significantly hinder fluid flow between locations on opposite longitudinal sides of the inflatable element. Typically, cleaning system 100 operates in a closed system environment.

During one state of operation, cleaning system 100 cleans the inner surface of the ventilation tube when ventilation tube-connector assembly 110 mediates a substantially air-tight seal between (i) the ventilator and/or an interior of ventilator port 164 and (ii) an interior of the ventilation tube and/or an interior of ventilation tube port 160.

Concurrently with maintaining of this ventilation machine-ventilator tube seal, inflatable element 188 may be positioned within the ventilation tube (e.g., in a distal portion of the ventilation tube), for example by moving a distal end of catheter main body 210 in a distal direction towards a distal end of the ventilation tube. For example, inflatable element 188 may be distally advanced when inflatable element 188 is in a non-contact state (i.e., not in contact with the inner surface of the ventilation tube). After inflatable element 188 is thus positioned, inflation of the inflatable element induces contact between an outer surface of inflatable element 188 and the inner surface of the ventilation tube and/or obstructs (i.e., significant hinders) longitudinal flow between proximal and distal portions of the interior of the ventilation tube.

Upon inflation of inflatable element 188 when the inflatable element is positioned within the ventilation tube, the inflated inflatable element forms a sliding boundary which obstructs (i.e., significantly hinders) fluid flow to between: (a) a more proximal portion of an interstitial region outside of catheter main body 210 and within the ventilation tube and (b) locations within the ventilation tube that are distal to the slidable boundary formed and delineated by inflatable element 188. This slidable boundary between the proximal and distal portions may be useful for facilitating the cleaning of the inner surface of the ventilation tube (by wiping), for example for substantially confining locations of negative pressure and/or fluid (e.g., pressurized fluid) introduced into an interstitial region outside of catheter main body 210 and within the ventilation tube so that the suction is introduced predominantly in the proximal portion of the ventilation tube.

Distal portion 212 of cleaning catheter 200 is shaped so as to define one or more distal suction orifices 140, typically through a lateral wall of distal portion 212. Typically, the one or more distal suction orifices 140 are located along distal portion 212 at one or more respective locations proximal to inflatable element 188. Typically, at least one of distal suction orifices 140 (such as all of the one or more distal suction orifices 140) is located within 1 cm of inflatable element 188, such as within 0.8 cm, e.g., within 0.5 cm of the inflatable element. For some applications, distal suction orifices 140 have a total cross-sectional area in aggregate of at least 2 mm2, no more than 25 mm2, and/or between 2 and 25 mm2, such as at least 4 mm2, no more than 16 mm2, and/or between 4 and 16 mm2.

Distal suction orifices 140 are supplied with negative pressure by the suction source and facilitate cleaning of the inner surface of the ventilation tube. For some applications, material within the interior of the ventilation tube may be suctioned into distal suction orifices 140 and proximally transported out of the ventilation tube, e.g., to a location that is proximal to ventilation tube-connector assembly 110. As described below in detail, fluid communication between the suction source and the one or more distal suction orifices 140 is provided by suction-orifice lumen 130. As used in the present application, including in the claims, "fluid communication" includes both positive and negative pressure fluid communication, and thus includes, for example, communication of a positive pressure or of a suction force.

For some applications, cleaning system 100 comprises a substantially impermeable and/or pliable sleeve 144 for protecting an outer surface of catheter main body 210. For some applications, a length of proximal portion 214 may be modified by sliding, in a proximal or distal direction, catheter main body 210 through ventilation tube-connector assembly 110.

Reference is still made to FIGS. 2A-D, 3A-D, and 4A-D. As mentioned above, in some configurations proximal input portion 216 of catheter main body 210 is configured to be inserted into or is disposed within, and axially slidable with respect to, input module 156.

Input module 156 is coupled to cleaning catheter 200, and comprises:

- an inflation module 150, which comprises an inflation chamber 155 (separate from the suction source);
- a flow regulator 170, which is (a) shaped so as to define suction port 146, which is coupleable in fluid communication with the suction source, and coupled in fluid communication with the suction source during use of cleaning system 100 (closed suction cleaning systems 300, 400, and 500 comprise flow regulator 370, 470, and 570, respectively, which are respective implementations of flow regulator 170);
- a plurality of mechanical user-control buttons 172; and
- typically, a housing 168, which encases proximal input portion 216 of catheter main body 210 and is shaped so as to define an internal channel (closed suction cleaning systems 300, 400, and 500 comprise housings 368, 468, and 568, respectively, which are respective implementations of housing 168).

Typically, the plurality of mechanical user-control buttons 172 comprise a mechanical inflation-chamber-control button 174, which is configured to:

- assume (a) at least a first spatial position when not depressed, such as shown in FIGS. 1, 2A, 2D, 3A, 3D, 4A, and 4D, and (b) a second spatial position when fully depressed, such as shown in FIGS. 2B-C, 3B-C, and 4B-C, and
- mechanically and non-electrically cause an increase in pressure in an interior of inflation chamber 155 during a transition of mechanical inflation-chamber-control button 174 from its first spatial position toward its second spatial position (a maximum increase in pressure is obtained if mechanical inflation-chamber-control button 174 is transitioned all the way from its first spatial position to its second spatial position).

Typically, the plurality of mechanical user-control buttons 172 further comprise one or more non-inflation-chamber-control buttons 176 (such as exactly one non-inflation-chamber-control button 176, as shown), which are not configured upon depression thereof to cause the increase in pressure in the interior of inflation chamber 155.

As mentioned above, mechanical inflation-chamber-control button 174 is configured to mechanically and non-electrically increase pressure in an interior of inflation chamber 155 during at least a portion of the transition of mechanical inflation-chamber-control button 174 from its first spatial position to its second spatial position. For some applications, mechanical inflation-chamber-control button 174 is configured to mechanically and non-electrically increase the pressure in the interior of inflation chamber 155 during an entirety of the transition of mechanical inflation-chamber-control button 174 from the its first spatial position to its second spatial position.

Reference is still made to FIGS. 2A-D, 3A-D, and 4A-D. For some applications, mechanical inflation-chamber-control button 174 is configured to increase the pressure in the interior of inflation chamber 155 by mechanically and non-electrically compressing inflation chamber 155 during the at least a portion of the transition of mechanical inflation-chamber-control button 174 from its first spatial position to its second spatial position. For some of these applications, inflation chamber 155 transitions from a lower level of compression to a higher level of compression during the at least a portion of the transition of mechanical inflation-chamber-control button 174 from its first spatial position to its second spatial position, and input module 156 is configured to elastically bias inflation chamber 155 toward the lower level of compression. For example, inflation module 150 may be elastically biased toward the lower level of compression, such as by the one or more springs mentioned below. Alternatively or additionally, for some applications, inflation chamber 155 (e.g., at least one wall of inflation chamber 155) is elastically biased toward the lower level of compression. For example, the at least one wall of inflation chamber 155 may be accordion-shaped and/or the chamber walls comprise an elastic material, such as silicon, rubber, or polyurethane. In some embodiments, substantially no friction needs to be overcome during expansion of inflation chamber 155. Alternatively or additionally, inflation module 150 (such as inflation chamber 155) comprises a distinct elastic element (e.g., a spring) that is arranged to bias inflation chamber 155 toward the lower level of compression. Alternatively or additionally, mechanical inflation-chamber-control button 174 is elastically biased toward the lower level of compression (and to the first configuration), for example by a spring. In any event, typically, when mechanical inflation-chamber-control button 174 is released, inflation chamber 155 expands. In other words, input module 156 is biased to assume the first configuration and first fluid-control state when in a resting state, such that inflation chamber 155 is in an expanded state when input module 156 is in the resting state.

For some applications, inflation chamber 155 comprises an elastic compartment, and input module 156 is configured such that the transition of mechanical inflation-chamber-control button 174 from its first spatial position to its second spatial position compresses the elastic compartment, thereby mechanically and non-electrically causing the increase in the pressure in an interior of the elastic compartment.

For some applications, mechanical inflation-chamber-control button 174 is configured to cause the increase in the pressure in the interior of inflation chamber 155 by mechanically and non-electrically compressing inflation chamber 155 during the at least a portion of the transition of mechanical inflation-chamber-control button 174 from its first spatial position to its second spatial position. For some of these applications, inflation chamber 155 transitions from a lower level of compression to a higher level of compression during the at least a portion of the transition of mechanical inflation-chamber-control button 174 from its first spatial position to its second spatial position, and wherein input module 156 is configured to elastically bias inflation chamber 155 toward the lower level of compression. Optionally, inflation module 150 is elastically biased toward the lower level of compression.

Typically, suction port 146 is shaped as a conventional suction port in accordance with hospital standards for coupling to standard hospital suctions sources. For example, suction port 146 may have a male conical interface. Typically, suction port 146 has a lumen size that corresponds with the lumen size of conventional tracheal suction lumens, which generally having a gauge of between 5 Fr to 18 Fr.

For some applications, input module 156 further comprises a user signal generator, which is configured to generate a user signal (e.g., a sound) during at least a portion of a period of fluid flow into inflation chamber 155 and/or during or upon deflation of inflatable element 188. The user signal generator may be electrical and/or mechanical.

For some applications, inflation chamber 155 has a volume of at least 1 cc, no more than 10 cc, and/or between 1 and 10 cc (e.g., at least 1.5 cc, no more than 3 cc, and/or between 1.5 and 3 cc), when mechanical inflation-chamber-control button 174 is in its first spatial position (i.e., not compressed). The volume typically equals more than 1.25 times (e.g., more than 1.5 times, or more than 2 times) and less than 3 times the volume of inflatable element 188. Typically, when mechanical inflation-chamber-control button 174 is in its second spatial position compressed), inflation chamber 155 has a volume of at least 1 cc less than when mechanical inflation-chamber-control button 174 is in its first spatial position (i.e., not compressed). Alternatively or additionally, for some applications, a volume of inflation chamber 155 when mechanical inflation-chamber-control button 174 is in its first spatial position is at least 25% greater (e.g., at least 50% greater, such as at least 100% greater) than a volume of the interior of inflatable element 188 when the pressure within inflatable element 188 equals 25 cm H2O.

For some applications, the one or more non-inflation-chamber-control buttons 176 comprise a mechanical suction-control button 178, which is configured to assume (a) at least a first spatial position when not depressed, such as shown in FIGS. 1, 2A, 2C, 3A, 3C, 4A, and 4C, and (b) a second spatial position when fully depressed, such as shown in FIGS. 2B, 3B, 4B, and 4D.

Figure 2A:
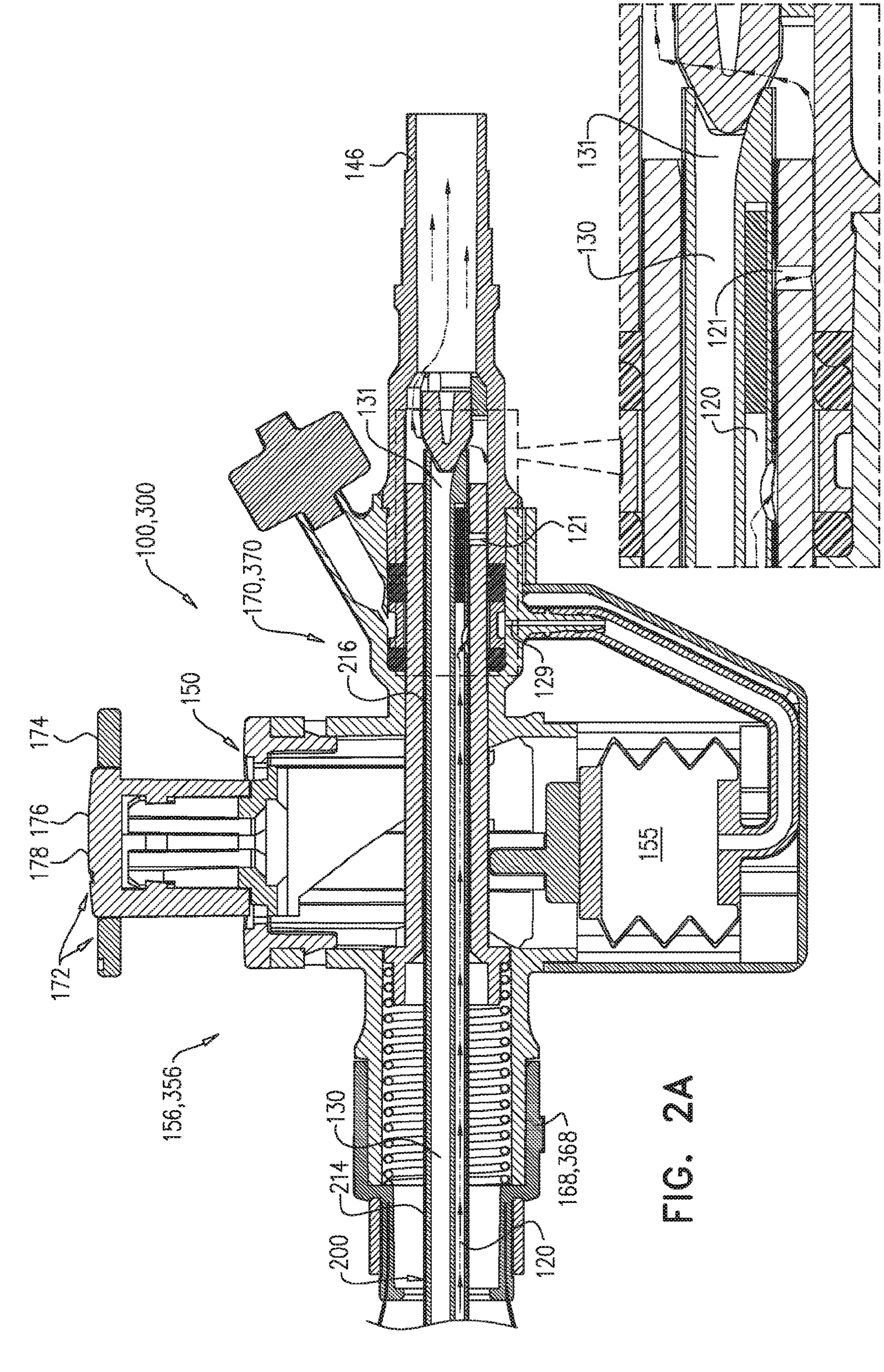
FIGS. 2A-D are schematic cross-sectional illustrations of a configuration of the closed suction cleaning system of FIG. 1 in respective states, in accordance with an application of the present invention.
Figure 2B:
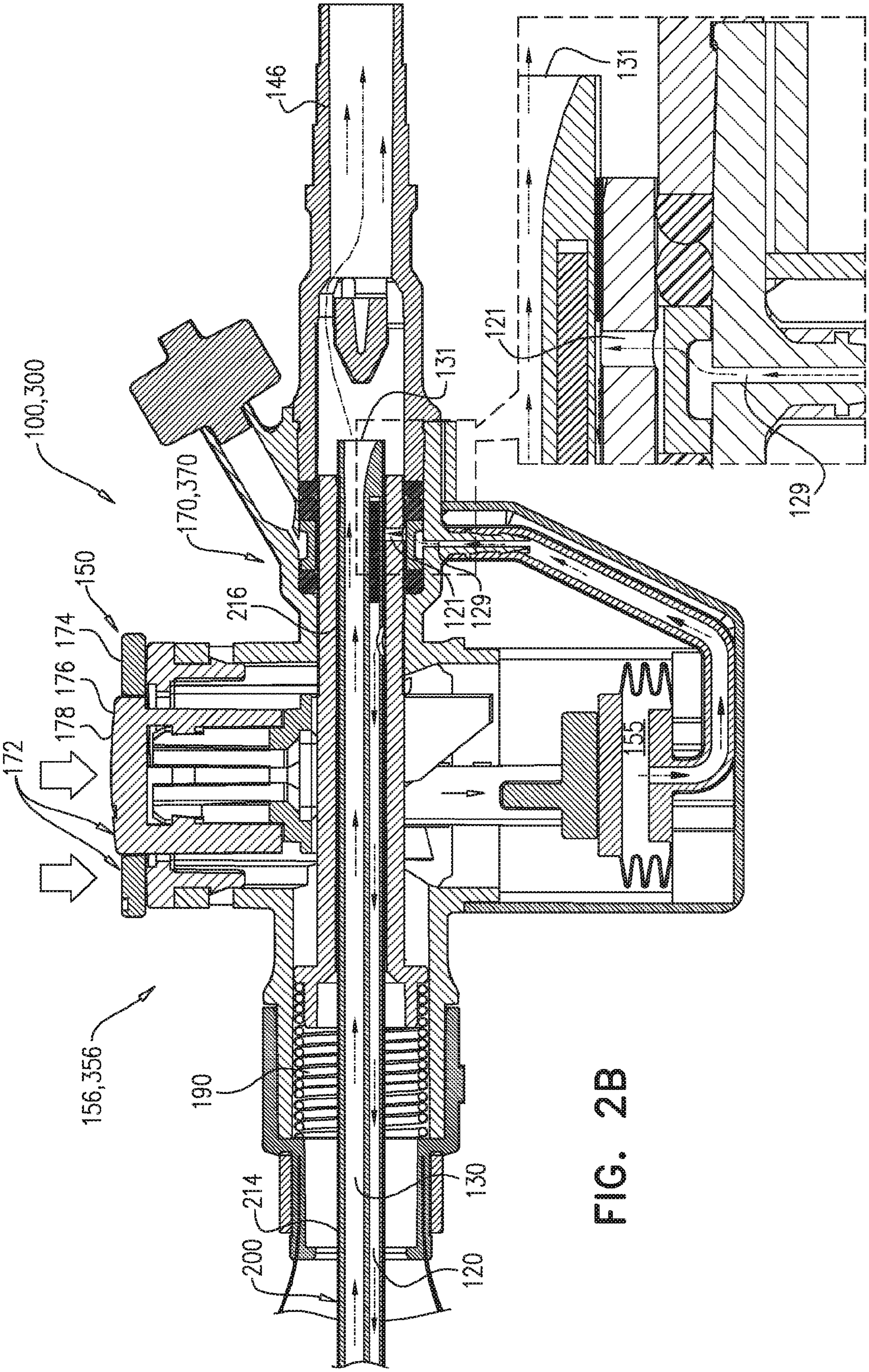
Figure 2C:
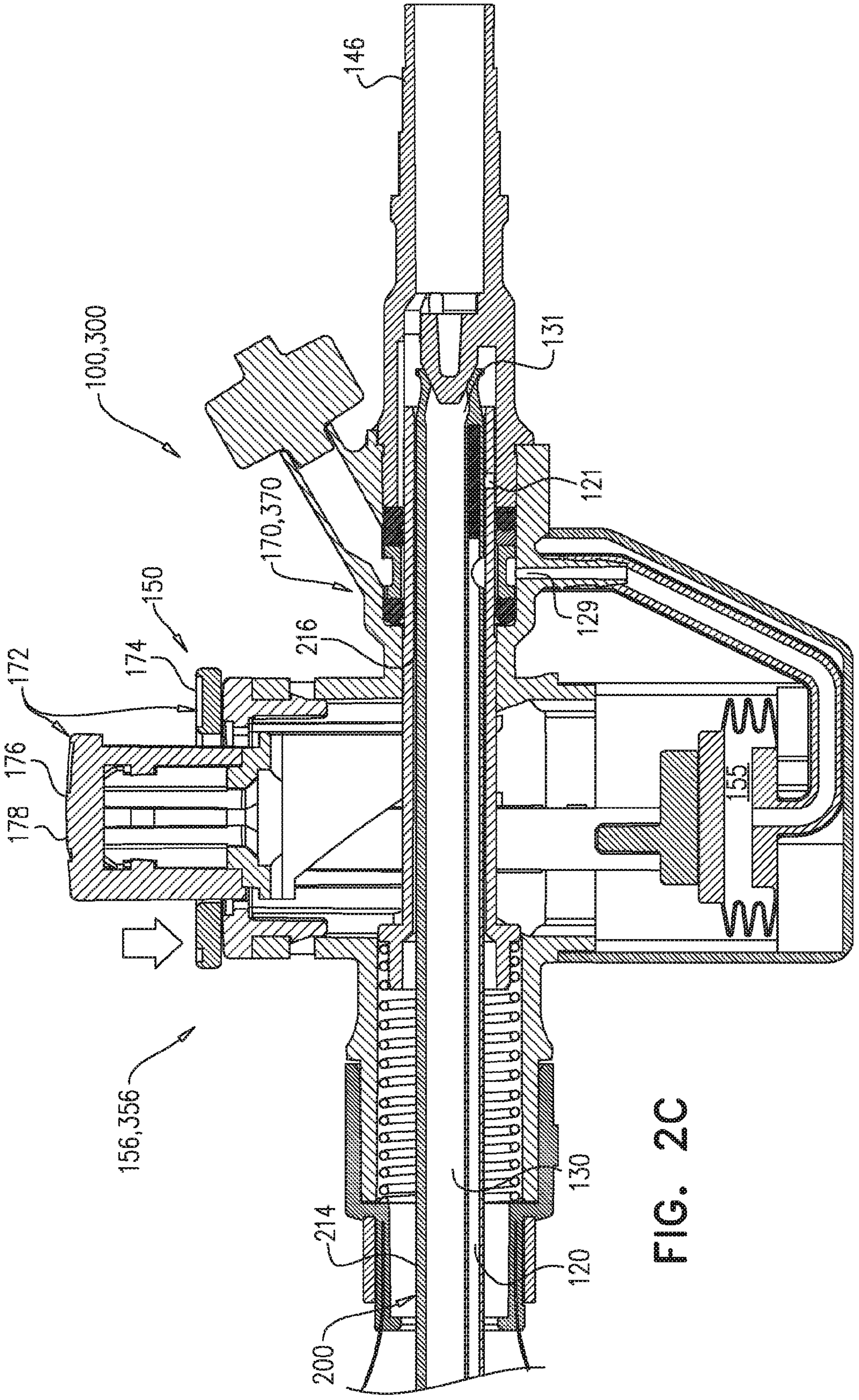
Figure 3A:
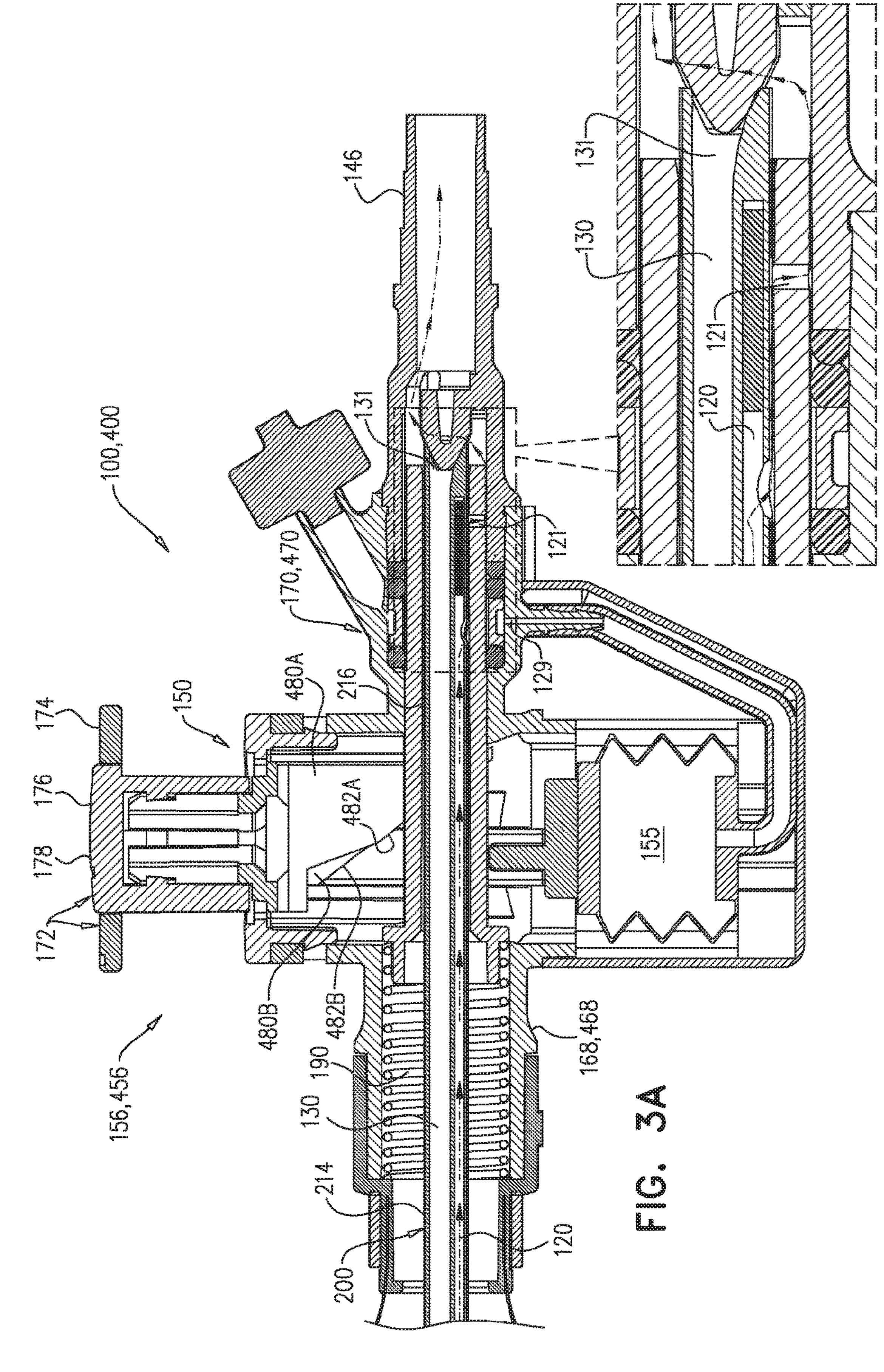
FIGS. 3A-D are schematic cross-sectional illustrations of another configuration of the closed suction cleaning system of FIG. 1 in respective states, in accordance with an application of the present invention.
Figure 3B:
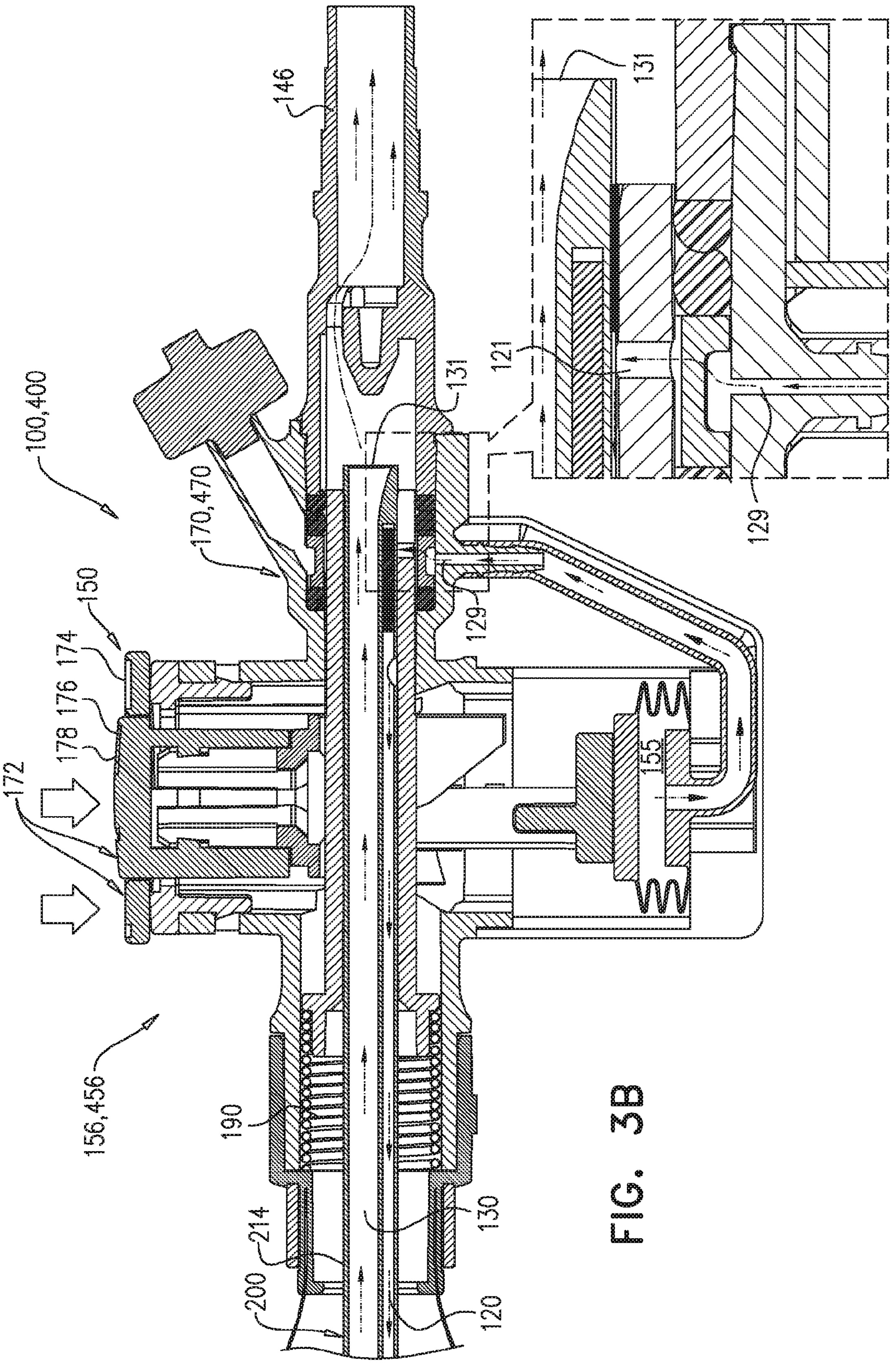
Figure 3C:
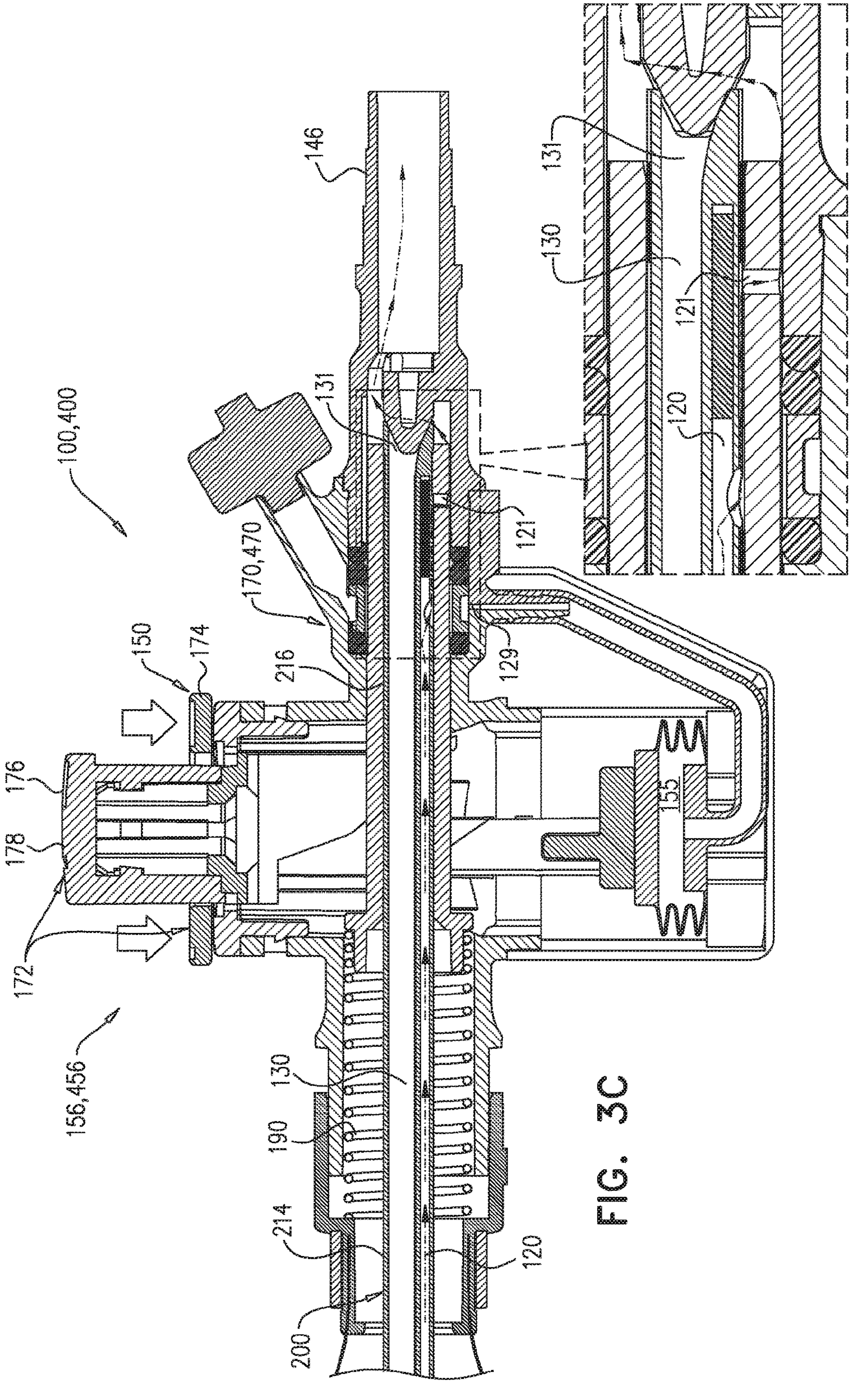
Figure 4A:
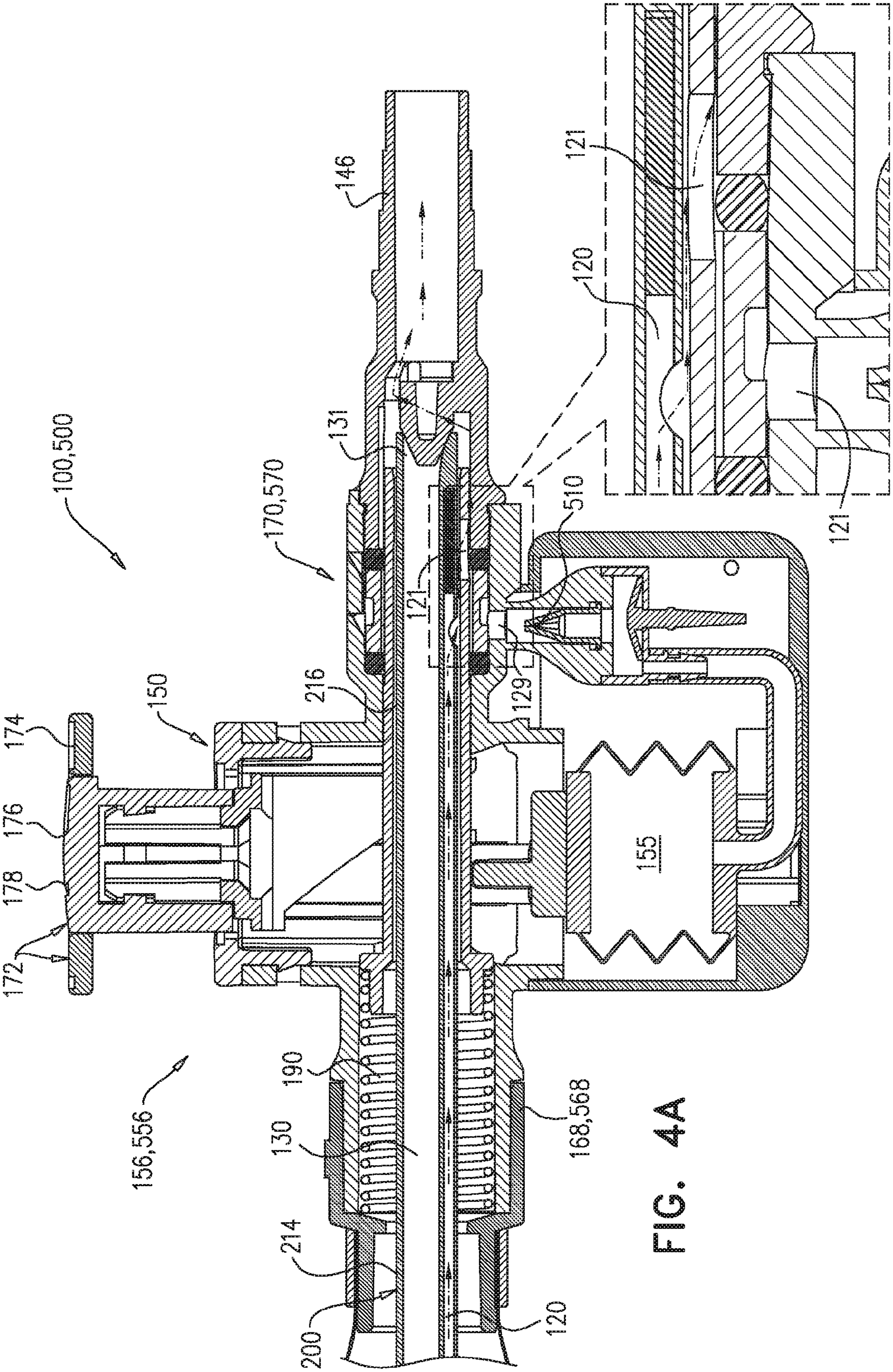
FIGS. 4A-D are schematic cross-sectional illustrations of yet another configuration of the closed suction cleaning system of FIG. 1 in respective states, in accordance with an application of the present invention.
Figure 4B:
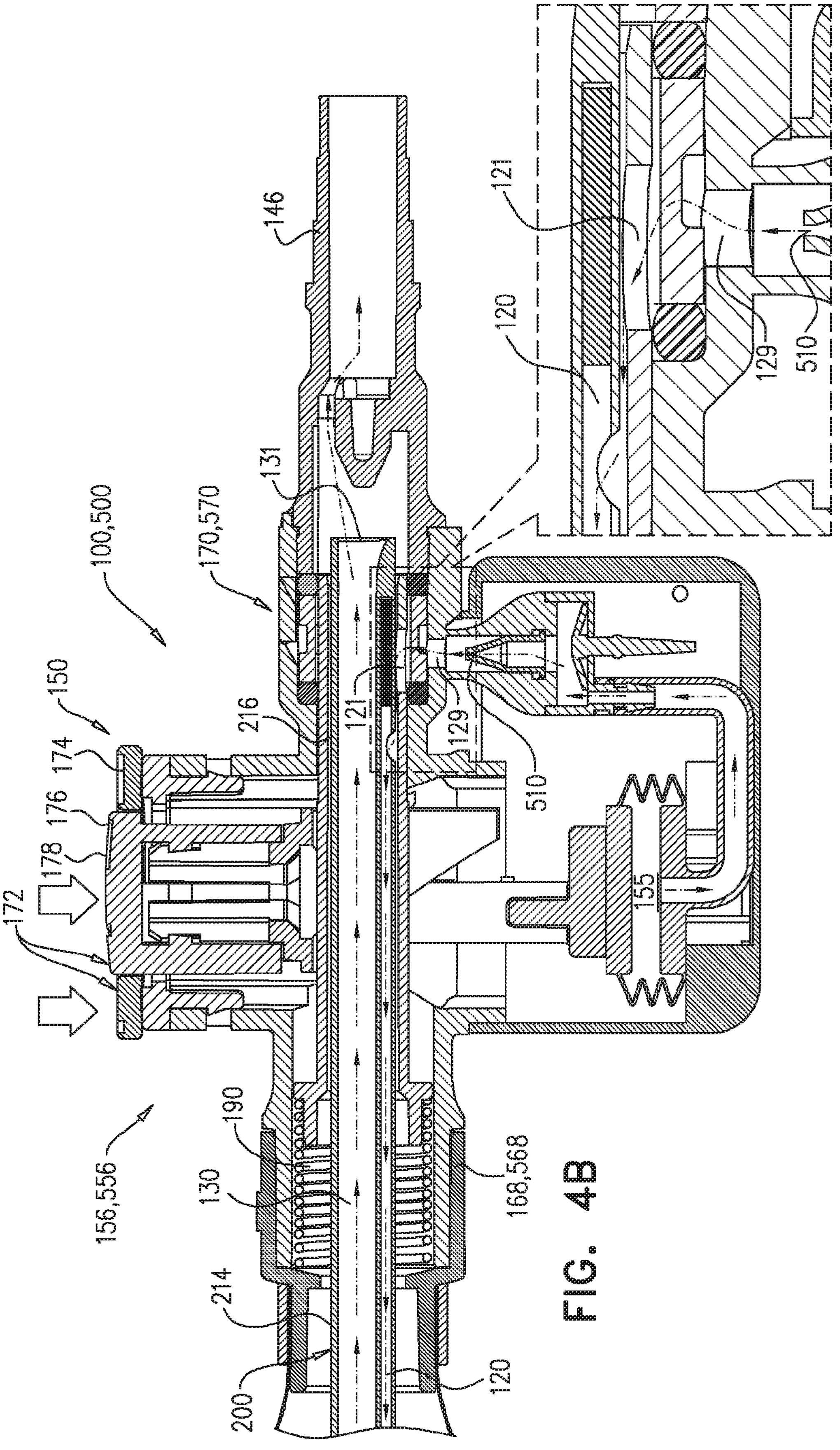

For some applications, input module 156 is arranged such that:

- when mechanical suction-control button 178 is in its first spatial position, such as shown in FIGS. 1, 2A, 2C, 3A, 3C, 4A, and 4C, flow regulator 170 (a) blocks fluid communication between the suction source and the one or more distal suction orifices 140, and (b) enables fluid communication between the suction source and the interior of inflatable element 188 via inflatable-element lumen 120, thereby, deflating and/or maintaining deflation of inflatable element 188, and
- when mechanical suction-control button 178 is in its second spatial position, such as shown in FIGS. 2B, 3B, and 4B, flow regulator 170 blocks fluid communication between the suction source and the interior of inflatable element 188.

Typically, mechanical suction-control and inflation-chamber-control buttons 178 and 174 are positioned on input module 156 such that when mechanical suction-control and inflation-chamber-control buttons 178 and 174 are in their respective first spatial positions, such as shown in FIGS. 1, 2A, 3A, and 4A, mechanical suction-control and inflation-chamber-control buttons 178 and 174 can be depressed and transitioned to their respective second spatial positions by application of a force to mechanical suction-control and inflation-chamber-control buttons 178 and 174 by a single 1 cm-by-2 cm rectangular surface, and, likewise, by an adult human finger. As used in the present application, including in the claims, a rectangular surface is flat. Typically, to enable such depression by a single finger, mechanical suction-control and inflation-chamber-control buttons 178 and 174 are disposed on the same side of input module 156. Alternatively, the two buttons are disposed on opposite sides of input module 156, in which case more than one finger, or one finger and the palm of the hand, must be used to depress the two buttons.

Reference is still made to FIGS. 2A-D, 3A-D, and 4A-D. Typically, mechanical suction-control and inflation-chamber-control buttons 178 and 174 are independent of each other in one or more of the following ways:

- input module 156 is arranged such that depression of one of the mechanical suction-control and inflation-chamber-control buttons 178 and 174 does not automatically cause depression, by input module 156, of the other of mechanical suction-control and inflation-chamber-control buttons 178 and 174;
- input module 156 is arranged such that depression of mechanical suction-control button 178 does not cause an increase in pressure in the interior of inflation chamber 155 during a transition of mechanical suction-control button 178 from its first spatial position toward its second spatial position; and/or
- input module 156 is arranged such that depression of mechanical inflation-chamber-control button 174 does not cause connection of the suction source in fluid communication with the one or more distal suction orifices 140 via suction-orifice lumen 130 during a transition of mechanical inflation-chamber-control button 174 from its first spatial position toward its second spatial position.

Reference is still made to FIGS. 2A-D, 3A-D, and 4A-D. For some applications, input module 156 is arranged such that during simultaneous depression of mechanical suction-control and inflation-chamber-control buttons 178 and 174, a resulting simultaneous transition of mechanical suction-control and inflation-chamber-control buttons 178 and 174 from their respective first spatial positions to their respective second spatial positions causes flow regulator 170 to:

- connect the suction source in fluid communication with the one or more distal suction orifices 140 via suction-orifice lumen 130, and
- connect the interior of inflation chamber 155 in fluid communication with the interior of inflatable element 188 via inflatable-element lumen 120, thereby inflating inflatable element 188, while maintaining the suction source in fluid communication with the one or more distal suction orifices 140 via suction-orifice lumen 130.

Depending, for example, on the relative heights of mechanical suction-control and inflation-chamber-control buttons 178 and 174, flow regulator 170 may either:

- first connect the suction source in fluid communication with the one or more distal suction orifices 140, and thereafter connect the interior of inflation chamber 155 in fluid communication with the interior of inflatable element 188; this may occur, for example, if mechanical suction-control button 178 is slightly higher than inflation-chamber-control button 174 when the buttons are in their respective first spatial position, or
- simultaneously connect the suction source in fluid communication with the one or more distal suction orifices 140, and the interior of inflation chamber 155 in fluid communication with the interior of inflatable element 188

For some applications, input module 156 is arranged such that during simultaneous depression of mechanical suction-control and inflation-chamber-control buttons 178 and 174, a resulting simultaneous transition of mechanical suction-control and inflation-chamber-control buttons 178 and 174 from their respective first spatial positions to their respective second spatial positions causes flow regulator 170:

- first, to disconnect the suction source from the fluid communication with the interior of inflatable element 188, and
- thereafter, to connect the interior of inflation chamber 155 in fluid communication with the interior of inflatable element 188 via inflatable-element lumen 120, thereby inflating inflatable element 188, while maintaining the suction source in fluid communication with the one or more distal suction orifices 140 via suction-orifice lumen 130.

For some applications, mechanical suction-control button 178 and/or mechanical inflation-chamber-control button 174 are biased toward their respective first spatial positions. To this end, for some applications input module 156 comprises one or more springs that are arranged to bias mechanical suction-control button 178 and mechanical inflation-chamber-control button 174 toward their respective first spatial positions, for example as described hereinabove. For some applications, input module 156 comprises an axially-oriented spring 190 (labeled in FIG. 2B), which is biased to proximally return proximal input portion 216 of catheter main body 210 to the base, resting state shown in FIGS. 2A, 3A, and 4A. Such proximal motion of proximal input portion 216 causes mechanical suction-control button 178 to return to its first spatial position. For some applications, input module 156 comprises exactly one spring that is arranged to bias both mechanical suction-control button 178 and mechanical inflation-chamber-control button 174 toward their respective first spatial positions.

Figure 2D:
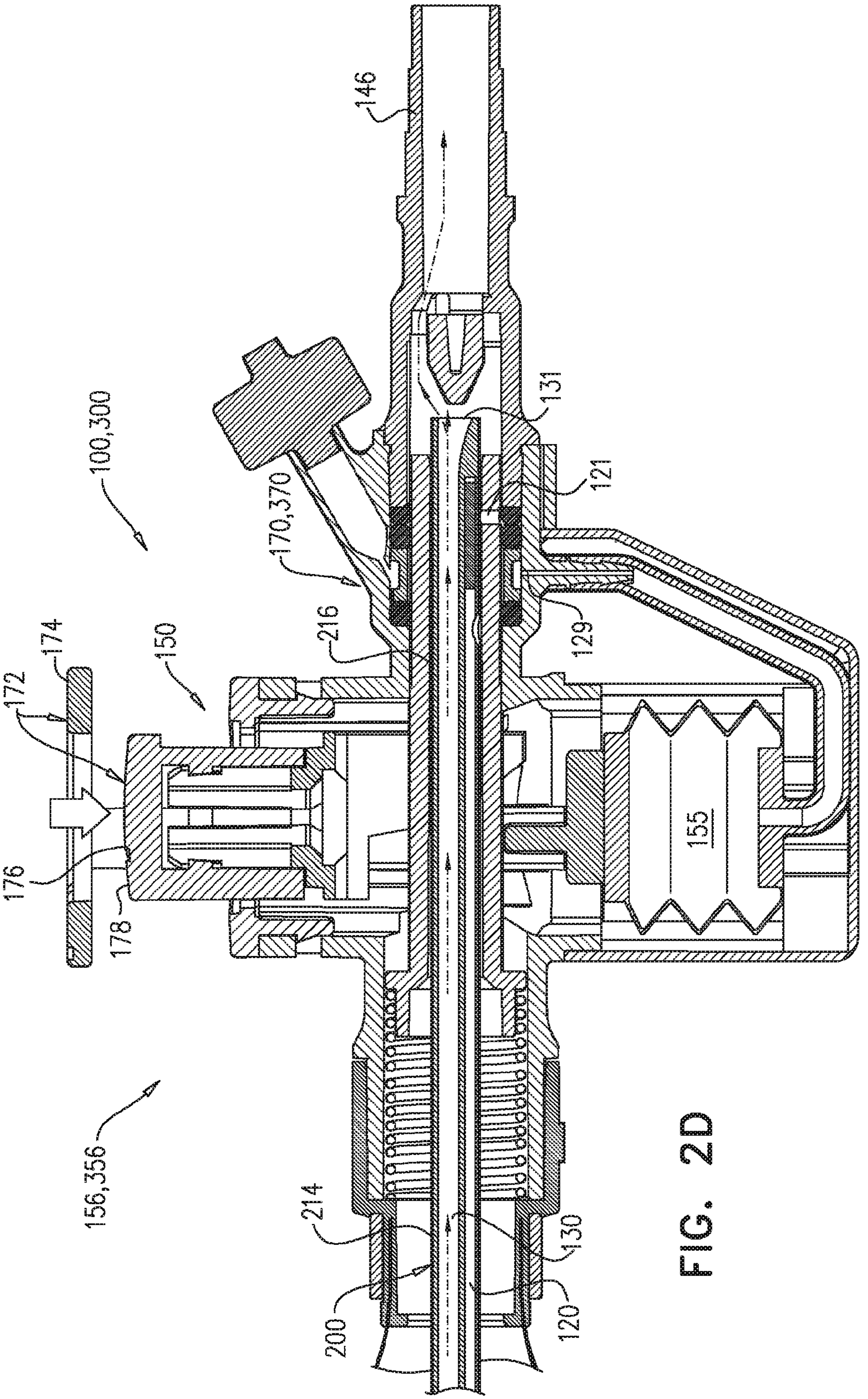
Figure 3D:
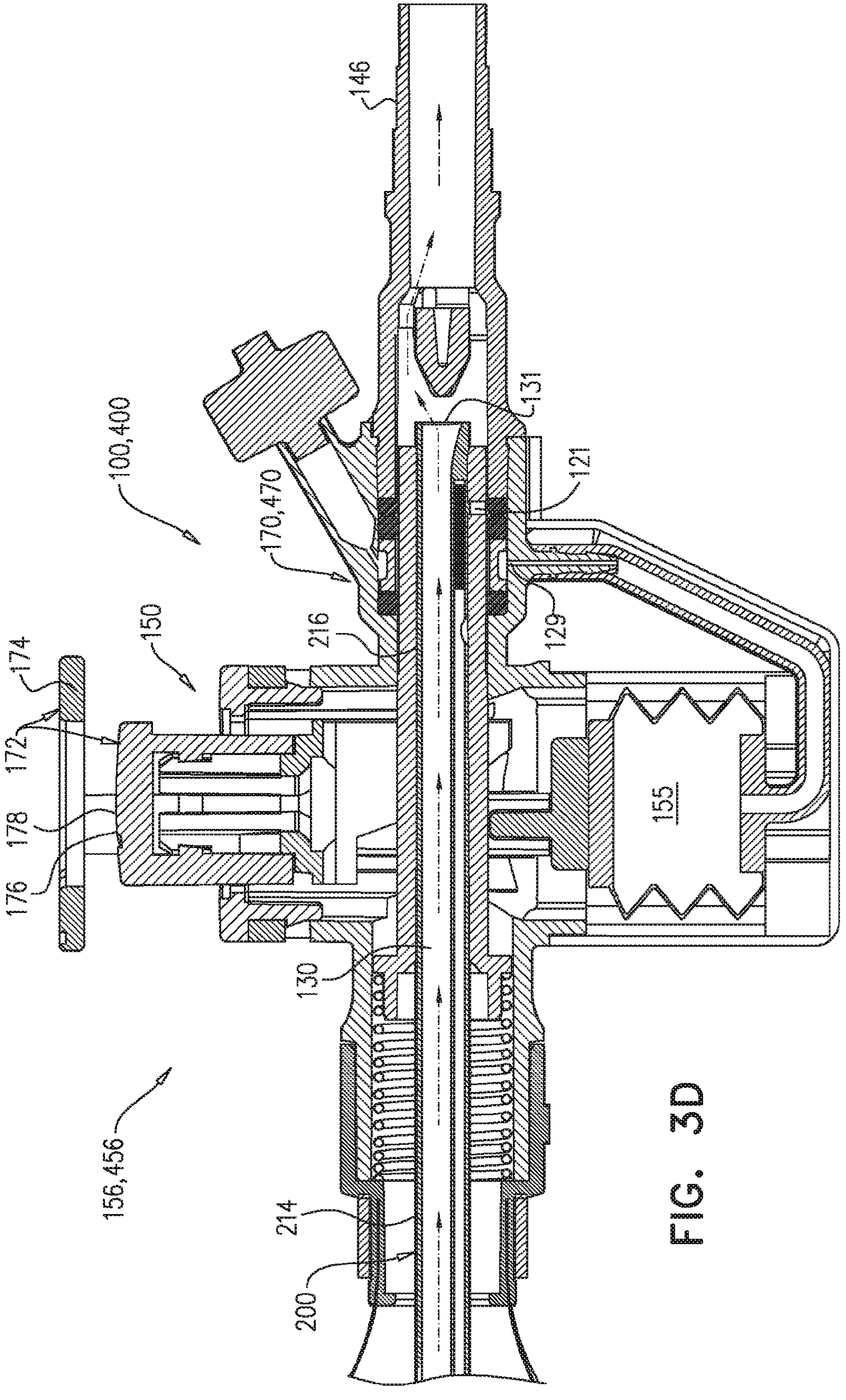
Figure 4C:
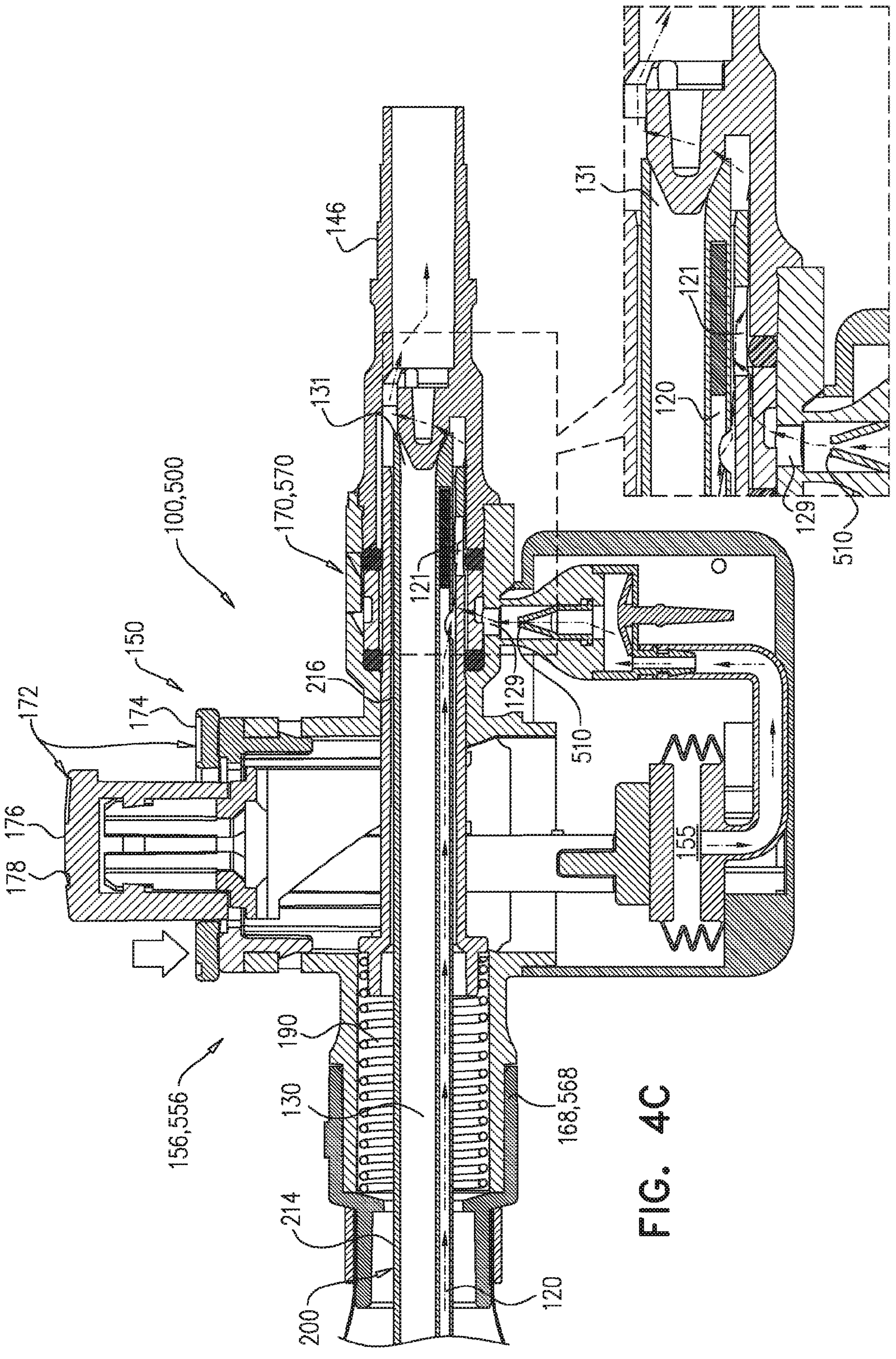
Figure 4D:
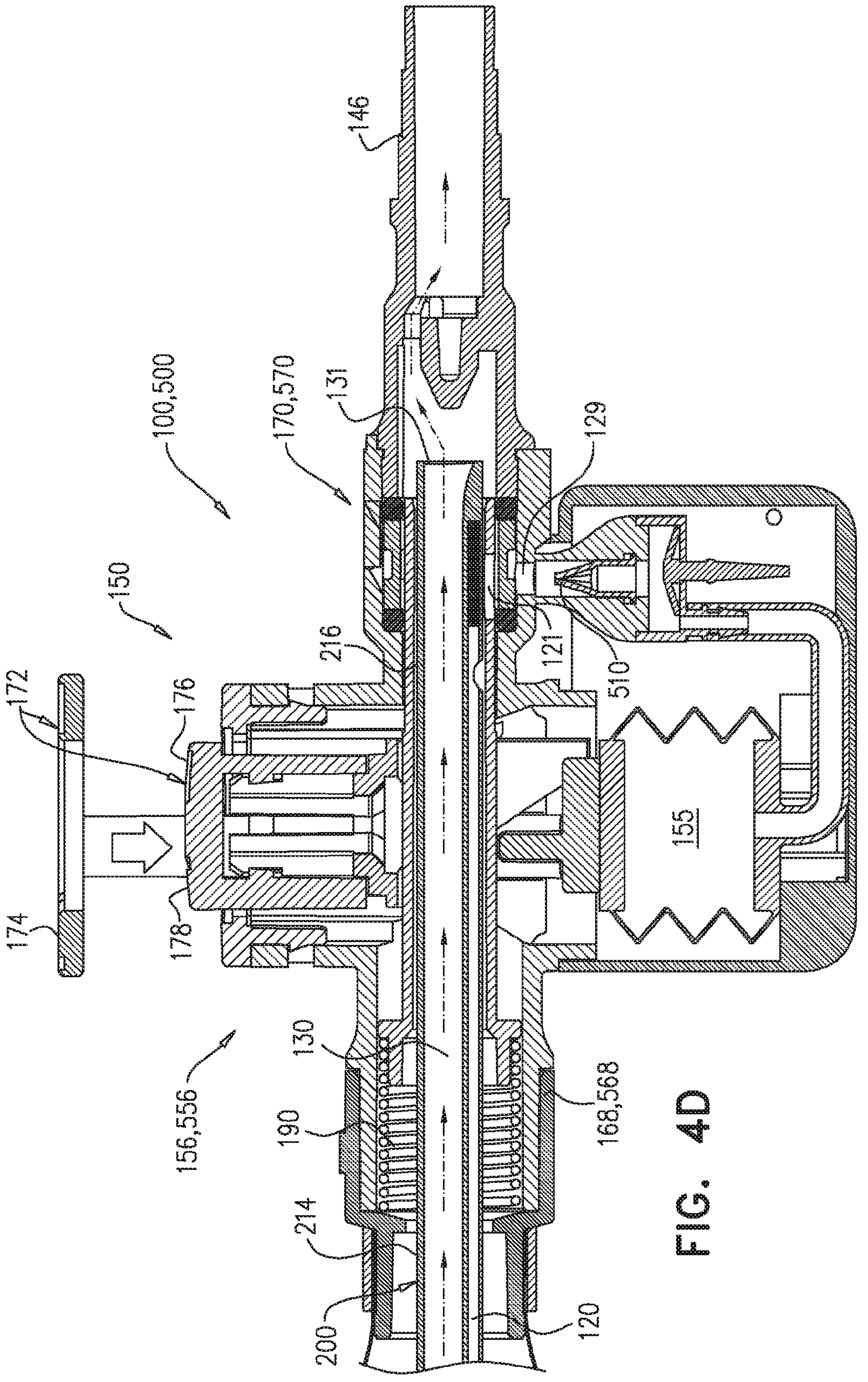

Reference is made to FIGS. 2D, 3D, and 4D. For some applications, input module 156 is arranged such that upon depression of mechanical suction-control button 178 and without depression of mechanical inflation-chamber-control button 174, flow regulator 170 enables fluid communication between the suction source and the one or more distal suction orifices 140 via suction-orifice lumen 130, without enabling fluid communication between the interior of inflation chamber 155 and the interior of inflatable element 188. This occurs:

- in the configurations shown in FIGS. 2D and 3D, because proximal inflation lumen inlet 121 is not axially aligned with respect to an exit port 129 of inflation chamber 155. Exit port 129 is in fluid communication with inflatable-element lumen 120 only when inflation lumen inlet 121 is aligned with exit port 129; and
- in the configuration shown in FIG. 4D, because there is no pressure increase in the interior of inflation chamber 155 to open one-way valve 510, described hereinbelow with reference to FIGS. 4A-D.

Reference is made to FIGS. 2A-B, 3A-B, and 4A-B. For cleaning a ventilation tube, the cleaning action typically comprises the following steps, which are typically performed in the following order:

- inserting cleaning catheter 200 into the ventilation tube in a proximal to distal direction while inflatable element 188 is essentially deflated by the suction applied to the interior thereof, such in the state shown in FIGS. 2A, 3A, and 4A;
- applying suction and inflating inflatable element 188 at a location near the distal end of the ventilation tube by transitioning input module 156 to the state shown in FIGS. 2B, 3B, and 4B, typically by simultaneously depressing mechanical suction-control and inflation-chamber-control buttons 178 and 174;
- withdrawing the catheter along the ventilation tube in a distal to proximal direction while inflatable element 188 is inflated and suction is applied to the one or more suction orifices, while input module 156 remains in the state shown in FIGS. 2B, 3B, and 4B; during such withdrawal, the inflated inflatable element wipes biofilm from the inner surface of the ventilation tube and the suction removes at least a portion of the wiped biofilm; and
- deflating inflatable element 188 when inflatable element 188 is near the proximal end of the ventilation tube or fully outside the proximal end of the ventilation tube, by transitioning input module 156 back to the state shown in FIGS. 2A, 3A, and 4A, by releasing mechanical suction-control and inflation-chamber-control buttons 178 and 174.

Reference is made to FIGS. 2A, 2D, 3A, 3D, 4A, and 4D. For some applications, cleaning system 100 may also be used for suctioning the trachea outside of and distal to the ventilation tube, typically by performing the following steps:

- inserting cleaning catheter 200 into the ventilation tube in a proximal to distal direction while inflatable element 188 is essentially deflated by the suction applied to the interior thereof, such in the state shown in FIGS. 2A, 3A, and 4A; typically, in order to perform "deep suction," the distal end of the cleaning catheter is advanced beyond the distal end of the ventilation tube; and
- applying suction to the trachea by transitioning input module 156 to the state shown in FIGS. 2D, 3D, and 4D, by depressing only mechanical suction-control button 178 without depressing inflation-chamber-control button 174.

For some applications, the distal end of catheter main body 210 is closed (such as shown). In these applications, tracheal suction is typically performed by advancing catheter main body 210 far enough beyond the distal end of the ventilation tube such that at least one of the one or more distal suction orifices 140 is in fluid communication with the interior of the trachea distally beyond the end of the ventilation tube. For other applications, catheter main body 210 is shaped so as to define, in addition to the one or more distal suction orifices 140, a distal-most suction orifice at a distal end of distal portion 212 of cleaning catheter 200, distal to inflatable element 188, for example such as described in above-mentioned U.S. Pat. No. 8,999,074, with reference to FIGS. 21A-B and 22A-C thereof.

Reference is made to FIGS. 2A-D. In this configuration, depression of mechanical suction-control button 178 alone controls the axial motion of proximal input portion 216 of catheter main body 210. Depression of inflation-chamber-control button 174 does not control the axial motion of proximal input portion 216. In particular, input module 456 and proximal input portion 216 are arranged such that:

- when mechanical suction-control button 178 is in its first spatial position (regardless of the spatial position of inflation-chamber-control button 174), proximal input portion 216 of catheter main body 210 is at a first axial position with respect to the internal channel of housing 368 of input module 356, such as shown in FIG. 2A; in this first axial position proximal input portion 216 (i) blocks fluid communication between the suction source and the one or more distal suction orifices 140, and (ii) connects the suction source in fluid communication with the interior of inflatable element 188, and during the depression of mechanical suction-control button 178, and the resulting transition of mechanical suction-control button 178 from its first spatial position to its second spatial position (regardless of the spatial position of inflation-chamber-control button 174), such as shown in FIG. 2B:

first, mechanical suction-control button 178 causes proximal input portion 216 to slide axially with respect to the internal channel from the first axial position to a second axial position, in which second axial position proximal input portion 216 connects the suction source in fluid communication with the one or more distal suction orifices 140 via suction-orifice lumen 130, and thereafter, mechanical suction-control button 178 causes proximal input portion 216 to slide axially with respect to the internal channel from the second axial position to a third axial position, in which third axial position proximal input portion 216 (i) disconnects the suction source from fluid communication with the interior of inflatable element 188, and (ii) connects the interior of inflation chamber 155 in fluid communication with the interior of inflatable element 188.

Reference is made to FIGS. 3A-D. In this configuration, input module 456 and proximal input portion 216 are arranged such that:

when mechanical suction-control and inflation-chamber-control buttons 178 and 174 are in their respective first spatial positions, proximal input portion 216 of catheter main body 210 is at a first axial position with respect to the internal channel of housing 468 of input module 456, such as shown in FIG. 3A; in this first axial position proximal input portion 216 (i) blocks fluid communication between the suction source and the one or more distal suction orifices 140, and (ii) connects the suction source in fluid communication with the interior of inflatable element 188, and during the simultaneous depression of mechanical suction-control and inflation-chamber-control buttons 178 and 174, and the resulting simultaneous transition of mechanical suction-control and inflation-chamber-control buttons 178 and 174 from their respective first spatial positions to their respective second spatial positions, such as shown in FIG. 3B:

first, mechanical suction-control button 178 causes proximal input portion 216 to slide axially with respect to the internal channel from the first axial position to a second axial position, in which second axial position proximal input portion 216 connects the suction source in fluid communication with the one or more distal suction orifices 140 via suction-orifice lumen 130, and thereafter, mechanical inflation-chamber-control button 174 causes proximal input portion 216 to slide axially with respect to the internal channel from the second axial position to a third axial position, in which third axial position proximal input portion 216 (i) disconnects the suction source from fluid communication with the interior of inflatable element 188, and (ii) connects the interior of inflation chamber 155 in fluid communication with the interior of inflatable element 188.

To provide this sequence of axially sliding, respective actuators 480A and 480B may be connected to mechanical suction-control button 178 and mechanical inflation-chamber-control button 174, respectively, and actuators 480A and 480B may have respective slanted surfaces 482A and 482B (labeled in FIG. 3A). As the two buttons are depressed, slanted surface 482A first comes in contact with and axially slide a pin (not visible) that axially slides proximal input portion 216, and subsequently slanted surface 482B comes in contact with and axially slides the pin that axially slides proximal input portion 216.

Reference is made to FIGS. 4A-D. In this configuration, flow regulator 170 comprises a pressure-actuated one-way valve 510, such as a check valve. Input module 556 and proximal input portion 216 are arranged such that:

when mechanical suction-control and inflation-chamber-control buttons 178 and 174 are in their respective first spatial positions, such as shown in FIG. 4A, proximal input portion 216 of catheter main body 210 is at a first axial position with respect to the internal channel of housing 568 of input module 156, in which first axial position proximal input portion 216 (i) blocks fluid communication between the suction source and the one or more distal suction orifices 140, and (ii) connects the suction source in fluid communication with the interior of inflatable element 188, and during the simultaneous depression of mechanical suction-control and inflation-chamber-control buttons 178 and 174, and the resulting simultaneous transition of mechanical suction-control and inflation-chamber-control buttons 178 and 174 from their respective first spatial positions to their respective second spatial positions, such as shown FIG. 4B:

first, mechanical suction-control button 178 causes proximal input portion 216 to slide axially with respect to the internal channel from the first axial position to a second axial position, in which second axial position proximal input portion 216 connects the suction source in fluid communication with the one or more distal suction orifices 140 via suction-orifice lumen 130, and thereafter, the increase in pressure in the interior of inflation chamber 155 caused by the transition of mechanical inflation-chamber-control button 174 from its first spatial position toward its second spatial position causes pressure-actuated one-way valve 510 to open, thereby (i) disconnecting the suction source from fluid communication with the interior of inflatable element 188, and (ii) connecting the interior of inflation chamber 155 in fluid communication with the interior of inflatable element 188 via inflatable-element lumen 120.

Reference is again made to FIGS. 1, 2A-D, 3A-D, and 4A-D. For some applications, input module 156 is arranged such that if suction having a strength of 25 cm H2O and a flow rate of 4 cc/second is applied to suction port 146:

a pressure within inflatable element 188 is less than 25 cm H2O at two seconds after completing, and while maintaining, depression of mechanical inflation-chamber-control button 174 as far as possible (without breaking any elements) toward its second spatial position and without depression of any of the other mechanical user-control buttons 172 of input module 156 (including mechanical suction-control button 178).

(When mechanical inflation-chamber-control button 174 is depressed as far as possible toward its second spatial position without depression of any of the other mechanical user-control buttons 172, mechanical inflation-chamber-control button 174 may or may not be able to fully reach its second spatial position.)

This arrangement of input module 156 prevents accidental substantial inflation of inflatable element 188 without also applying suction to distal suction orifices 140. Such inflation without suction is not desirable because if the balloon were inflated and accidentally withdrawn along the ventilation tube without also applying suction to distal suction orifices 140, the biofilm wiped by inflatable element 188 from the inner surface of the ventilation tube would accumulate and be dragged up toward the ventilation connection rather than be removed from the ventilation circuit. This arrangement prevents such undesired inflation without the necessity of locking any of mechanical user-control buttons 172, including mechanical inflation-chamber-control button 174.

For some applications, the above-mentioned limitation of pressure with inflatable element 188 is achieved as follows for the different configurations described herein:

for the configuration shown in FIG. 2C, input module 356 is arranged such that upon depression of mechanical inflation-chamber-control button 174 as far as possible toward its second spatial position and without depression of any of the other mechanical user-control buttons 172 of input module 356 (including without depression of mechanical suction-control button 178), flow regulator 370 does not connect the interior of inflation chamber 155 in fluid communication with the interior of inflatable element 188; as a result, the pressurized air in inflation chamber 155 cannot be delivered to inflatable element 188;

for the configuration shown in FIG. 3C, input module 456 is arranged such that upon depression of mechanical inflation-chamber-control button 174 as far as possible toward its second spatial position and without depression of any of the other mechanical user-control buttons 172 of input module 456 (including without depression of mechanical suction-control button 178), flow regulator 470 does not connect the interior of inflation chamber 155 in fluid communication with the interior of inflatable element 188; as a result, the pressurized air in inflation chamber 155 cannot be delivered to inflatable element 188; and for the configuration shown in FIG. 4C, input module 556 is arranged such that when mechanical inflation-chamber-control button 174 is depressed as far as possible toward its second spatial position and without depression of any of the other mechanical user-control buttons 172 of input module 556 (including without depression of mechanical suction-control button 178), flow regulator 170 enables fluid communication between the interior of inflation chamber 155 and the interior of inflatable element 188 via inflatable-element lumen 120 (because the exit port of one-way valve 510 is typically always in fluid communication with inflatable-element lumen 120 in the configuration of FIGS. 4A-D, regardless of the axial position of proximal input portion 216 of cleaning catheter 200); however, because the interior of inflatable element 188 remains in fluid communication with the suction source via inflatable-element lumen 120, the air pressure applied from inflation chamber 155 to the interior of inflatable elements 188 is quickly (typically, within two seconds) offset by the suction applied by the suction source.

Figure 5:
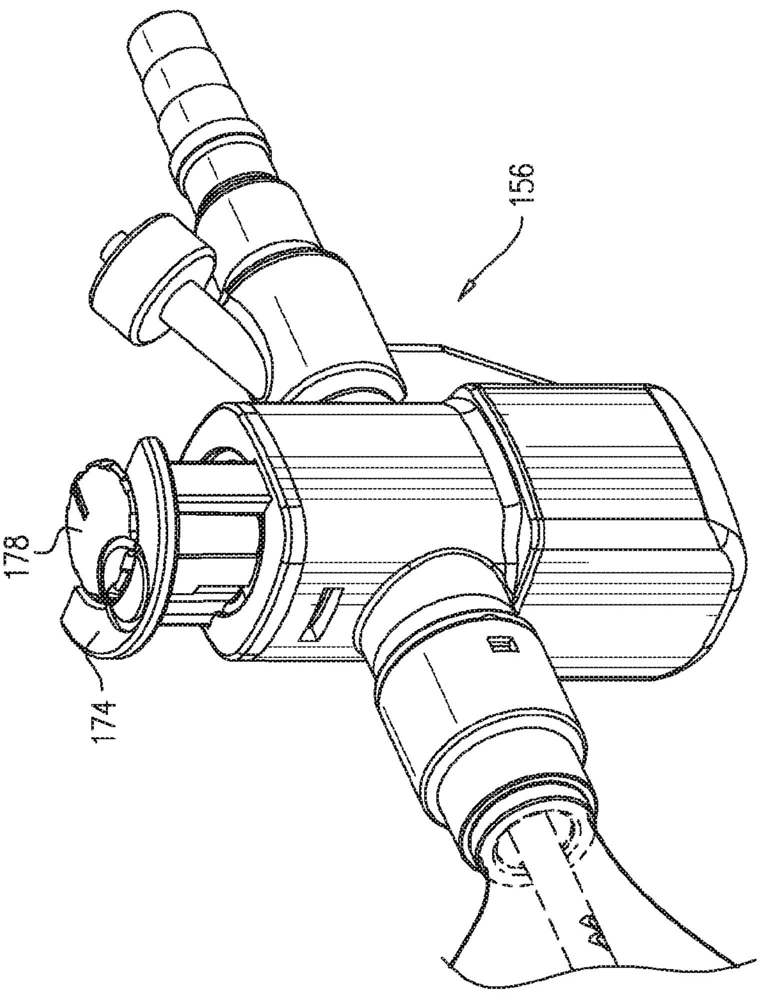
FIG. 5 is a schematic illustration of an alternative configuration of a mechanical inflation-chamber-control button of the closed suction cleaning system of FIG. 1, in accordance with an application of the present invention.

Reference is again made to FIG. 1, and is also made to FIG. 5, which is a schematic illustration of an alternative configuration of mechanical inflation-chamber-control button 174, in accordance with an application of the present invention. In the configuration shown in FIG. 1 (and FIGS. 2A-D, 3A-D, and 4A-D), mechanical inflation-chamber-control button 174 entirely surrounds mechanical suction-control button 178. In the configuration shown in FIG. 5, mechanical inflation-chamber-control button 174 only partially surrounds mechanical suction-control button 178 (e.g., surrounds between 50% and 75% of a perimeter of mechanical suction-control button 178). For example, mechanical inflation-chamber-control button 174 may be C-shaped, such as shown. Such partial surrounding may provide better ergonomic access to mechanical suction-control button 178 for a user's thumb, such as for depression of only mechanical suction-control button 178, such as shown in FIGS. 2D, 3D, and 4D. In addition, having the non-surrounded portion of mechanical suction-control button 178 facing proximally (generally to the right in the figures) may provide better ergonomic access to mechanical suction-control button 178 for the user, whose hand generally approaches input module 156 from a proximal direction.

Figure 6B:
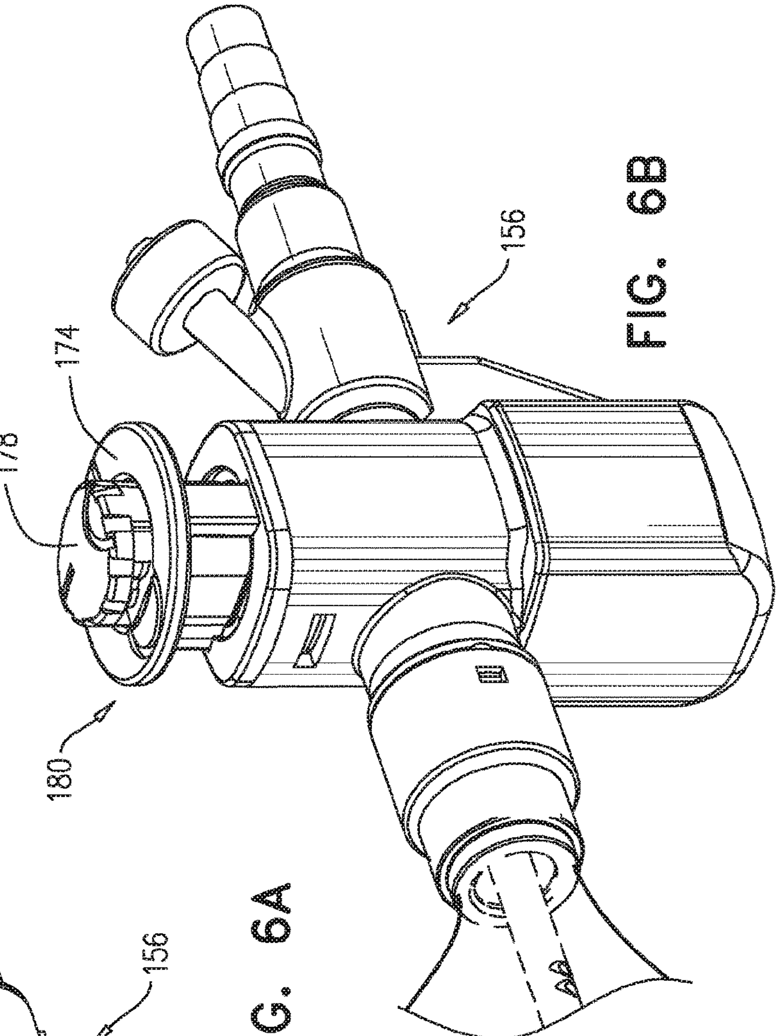
FIGS. 6A-B are schematic illustrations of a locking mechanism in unlocked and locked states, respectively, in accordance with an application of the present invention.
Figure 6A:
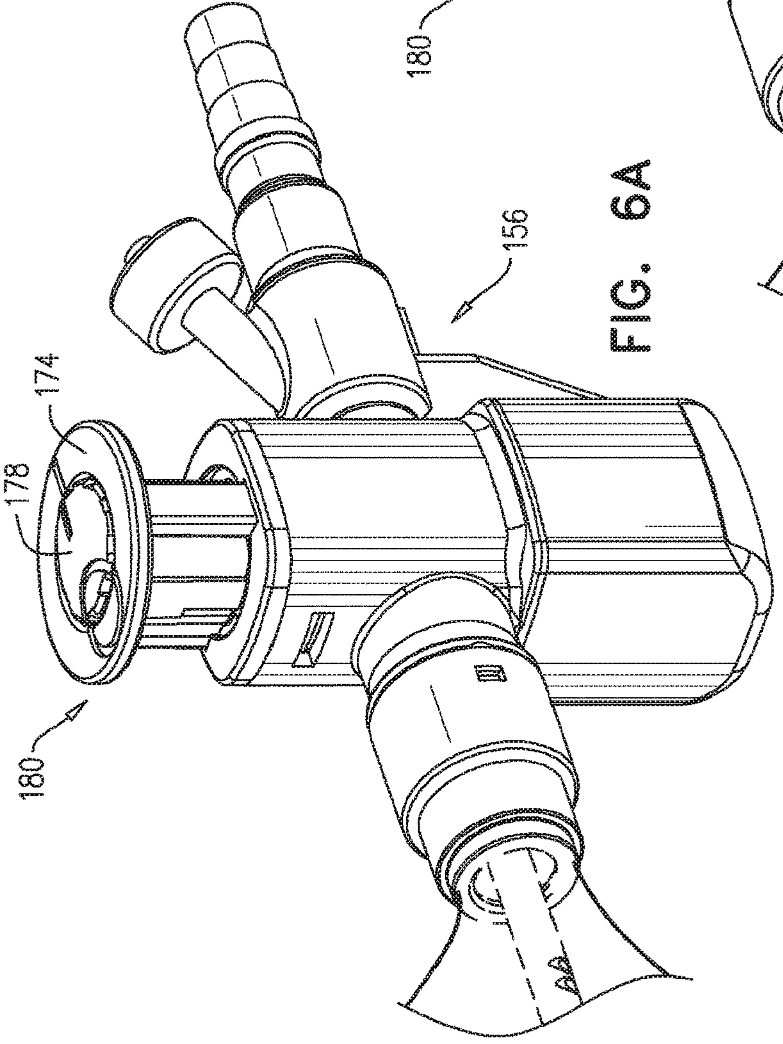

Reference is now made to FIGS. 6A-B, which are schematic illustrations of a locking mechanism 180 of input module 156 in unlocked and locked states, respectively, in accordance with an application of the present invention. When locking mechanism 180 is in the unlocked state, as shown in FIG. 6A, mechanical suction-control button 178 (and mechanical inflation-chamber-control button 174) can be depressed, as described hereinabove with reference to FIGS. 2B, 2D, 3B, 3D, 4B, and 4D. When locking mechanism 180 is in the locked state, as shown in FIG. 6B, mechanical suction-control button 178 cannot be depressed, but, typically, mechanical inflation-chamber-control button 174 can still be depressed, such as shown in FIGS. 2C, 3C, and 4C. Prevention of depression of mechanical suction-control button 178 by locking mechanism 180, even without preventing depression of mechanical inflation-chamber-control button 174, prevents inflation of inflammable element 188 for more than two seconds even if inflation-chamber-control button 174 is depressed, such as described hereinabove. For some applications, locking mechanism 180 is transitioned between the unlocked and locked states and vice versa by rotation of mechanical suction-control button 178.

Reference is again made to FIGS. 1, 2A-D, 3A-D, and 4A-D. In general it has been described herein that when a user simultaneously depresses mechanical suction-control and inflation-chamber-control buttons 178 and 174 (rather than gradually depressing one button after the other), the transition between the base state to the final state occurs in the following sequence:

(i) the suction source is connected in fluid communication with the one or more distal suction orifices 140;

(ii) the suction source is disconnected from fluid communication with the interior of inflatable element 188; and (iii) the interior of inflation chamber 155 is connected in fluid communication with the interior of inflatable element 188.

Indeed, this sequence of events may have certain clinical benefits.

However, one of ordinary skill in the art, having read the present application, will understand that this sequence of events may be readily modified by adjusting the placement of the inlets to the several lumens. While such modifications may be technically and/or clinically less desirable than the order described above, such modifications may not render cleaning system 100 non-operational, particularly if the user presses the buttons quickly.

For example, in the above sequence of events, there is a short transient state during which there is suction communication to both inflatable element 188 and the one or more distal suction orifices 140. However, a slight modification to the placement of the inlets would result in an alternate short transient state during which there is not suction communication with both inflatable element 188 and the one or more distal suction orifices 140, e.g.:

(i) the suction source is disconnected from fluid communication with the interior of inflatable element 188;

(ii) the suction source is connected in fluid communication with the one or more distal suction orifices 140; and (iii) the interior of inflation chamber 155 is connected in fluid communication with the interior of inflatable element 188.

Similarly, while it may be disadvantageous to begin inflating inflatable element 188 while the inflatable element is still in fluid communication with the suction source (since some of the inflating air is lost to the suction), such premature inflation, if it occurs as a brief transient state, may still be tolerated and maintain the device functionality.

Therefore, such minor alternate scenarios, although not elaborated upon herein, are simple to implement for one skilled in the art who has read the present application, and are included within the scope of the present invention. The claims should thus not be interpreted as being limited a particular order of events unless specified.

In the description and claims of the present application, each of the verbs, "comprise," "include" and "have," and conjugates thereof, are used to indicate that the object or objects of the verb are not necessarily a complete listing of members, components, elements or parts of the subject or subjects of the verb. The articles "a" and "an" are used herein to refer to one or to more than one (i.e., to at least one) of the grammatical object of the article. By way of example, "an element" means one element or more than one element. The term "including" is used herein to mean, and is used interchangeably with, the phrase "including but not limited to." The term "or" is used herein to mean, and is used interchangeably with, the term "and/or," unless context clearly indicates otherwise. The teem "such as" is used herein to mean, and is used interchangeably, with the phrase "such as but not limited to."

All publications, patent applications, patents, and other references mentioned herein are incorporated by reference in their entirety. In case of conflict, the present patent specification, including definitions, will prevail. In addition, the materials, methods, and examples are illustrative only and not intended to be limiting.

For brevity, some explicit combinations of various features are not explicitly illustrated in the figures and/or described. It is now disclosed that any combination of the method or device features disclosed herein can be combined in any manner—including any combination of features—any combination of features can be included in any embodiment and/or omitted from any embodiments.

The scope of the present invention includes embodiments described in the following applications, which are assigned to the assignee of the present application and are incorporated herein by reference. In an embodiment, techniques and apparatus described in one or more of the following applications are combined with techniques and apparatus described herein. It is noted that the phrase "fluid-control state" used herein may, for some applications, correspond in some respects to the phrases "mode," "activation mode," and/or "operating mode" referred to in the following applications (although many of the configurations of these states described herein differ in at least some respects from the configurations of the modes described in the following applications). It is also noted that the phrase "mechanical user control element" used herein may, for some applications, correspond in some respects to the word "switch," referred to in the following applications (although many of the configurations of these states described herein differ in at least some respects from the configurations of the modes described in the following applications):

PCT Publication WO/2012/131626 to Einav et al.

GB 2482618 A to Einav et al.;

UK Application GB 1119794.4, filed Nov. 16, 2011;

U.S. Provisional Application 61/468,990, filed Mar. 29, 2011;

U.S. Provisional Application 61/473,790, filed Apr. 10, 2011;

U.S. Provisional Application 61/483,699, filed May 8, 2011;

U.S. Provisional Application 61/496,019, filed Jun. 12, 2011;

U.S. Provisional Application 61/527,658, filed Aug. 26, 2011;

U.S. Provisional Application 61/539,998, filed Sep. 28, 2011;

U.S. Provisional Application 61/560,385, filed Nov. 16, 2011;

U.S. Provisional Application 61/603,340, filed Feb. 26, 2012;

U.S. Provisional Application 61/603,344, filed Feb. 26, 2012;

U.S. Provisional Application 61/609,763, filed Mar. 12, 2012;

U.S. Provisional Application 61/613,408, filed Mar. 20, 2012;

U.S. Provisional Application 61/635,360, filed Apr. 19, 2012;

U.S. Provisional Application 61/655,801, filed Jun. 5, 2012;

U.S. Provisional Application 61/660,832, filed Jun. 18, 2012;

U.S. Provisional Application 61/673,744, filed Jul. 20, 2012;

PCT Publication WO 2013/030821 to Zachar et al.;

U.S. Pat. No. 8,999,074 to Zachar et al;

UK Application 1600233.9, filed Jan. 6, 2016;

U.S. Provisional Application 62/287,223, filed Jan. 26, 2016;

U.S. Provisional Application 62/319,640, filed Apr. 7, 2016;

U.S. Provisional Application 62/336,894, filed May 16, 2016;

U.S. Provisional Application 62/336,753, filed May 16, 2016;

U.S. Provisional Application 62/376,102, filed Aug. 17, 2016;

U.S. application Ser. No. 15/363,782, filed Nov. 29, 2016;

International Application PCT/IL2016/051367, filed Dec. 22, 2016; and

U.S. application Ser. No. 15/595,250, filed May 15, 2017.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with a tracheal ventilation tube and a suction source, the apparatus comprising:

(A) a cleaning catheter, which is insertable into the ventilation tube and comprises:

(i) an elongate, flexible, tubular catheter main body, which is shaped so as to define (a) one or more distal suction orifices, (b) a suction-orifice lumen, and (c) an inflatable element lumen: and (ii) an inflatable element, which is mounted to the catheter main body, and which is shaped so as to define an interior that is in fluid communication with the inflatable-element lumen; and (B) an input module, which is coupled to the cleaning catheter, and comprises:

(i) an inflation module, which comprises an inflation chamber separate from the suction source;

(ii) a flow regulator, which is shaped so as to define a suction port coupleable in fluid communication with the suction source; and (iii) a plurality of mechanical user-control buttons, which comprise:

(1) a mechanical inflation-chamber-control button, which is configured to (a) assume at least a first spatial position when not depressed, and a second spatial position when fully depressed, and (b) mechanically and non-electrically cause an increase in pressure in an interior of the inflation chamber during a transition of the mechanical inflation-chamber-control button from its first spatial position toward its second spatial position; and (2) one or more non-inflation-chamber-control buttons, which are not configured upon depression thereof to cause the increase in pressure in the interior of the inflation chamber, wherein the input module is arranged such that, if suction having a strength of 25 cm $H_2O$ and a flow rate of 4 cc/second is applied to the suction port:

a pressure within the inflatable element is less than 25 cm $H_2O$ at two seconds after completing, and while maintaining, depression of the mechanical inflation-chamber-control button as far as possible toward its second spatial position and without depression of any of the other mechanical user-control buttons of the input module, wherein the input module is arranged such that upon depression of the mechanical inflation-chamber-control button as far as possible toward its second spatial position and without depression of any of the other mechanical user-control buttons of the input module, the flow regulator does not connect the interior of the inflation chamber in fluid communication with the interior of the inflatable element.

2. The apparatus according to claim 1, wherein a volume of the inflation chamber when the mechanical inflation-chamber-control button is in its first spatial position is at least 25% greater than a volume of the interior of the inflatable element when the pressure within the inflatable element equals 25 cm $H_2O$.

3. The apparatus according to claim 1, wherein the inflatable element is mounted to the catheter main body at a location within 3 cm of at least one of the one or more distal suction orifices.

4. The apparatus according to claim 1, wherein the suction port is coupled in fluid communication with the suction source.

5. The apparatus according to claim 1, wherein the inflation chamber has a volume of between 1 and 10 cc when the first mechanical control element is in its first spatial position.

6. The apparatus according to claim 1, wherein the mechanical suction-control button and the mechanical inflation-chamber-control button are biased toward their respective first spatial positions.

7. The apparatus according to claim 6, wherein the input module comprises one or more springs that are arranged to bias the mechanical suction-control button and the mechanical inflation-chamber-control button toward their respective first spatial positions.

8. The apparatus according to claim 7, wherein the input module comprises exactly one spring that is arranged to bias both the mechanical suction-control button and the mechanical inflation-chamber-control button toward their respective first spatial positions.

9. The apparatus according to claim 1, wherein the inflation chamber comprises an elastic compartment, and wherein the input module is configured such that the transition of the mechanical inflation chamber control button from its first spatial position to its second spatial position compresses the elastic compartment, thereby mechanically and non-electrically causing the increase in the pressure in an interior of the elastic compartment.

10. An apparatus for use with a tracheal ventilation tube and a suction source, the apparatus comprising:

(A) a cleaning catheter, which is insertable into the ventilation tube and comprises:

(i) an elongate, flexible, tubular catheter main body, which is shaped so as to define (a) one or more distal suction orifices, (b) a suction-orifice lumen, and (c) an inflatable element lumen: and (ii) an inflatable element, which is mounted to the catheter main body, and which is shaped so as to define an interior that is in fluid communication with the inflatable-element lumen; and (B) an input module, which is coupled to the cleaning catheter, and comprises:

(i) an inflation module, which comprises an inflation chamber separate from the suction source;

(ii) a flow regulator, which is shaped so as to define a suction port coupleable in fluid communication with the suction source; and (iii) a plurality of mechanical user-control buttons, which comprise:

(1) a mechanical inflation-chamber-control button, which is configured to (a) assume at least a first spatial position when not depressed, and a second spatial position when fully depressed, and (b) mechanically and non-electrically cause an increase in pressure in an interior of the inflation chamber during a transition of the mechanical inflation-chamber-control button from its first spatial position toward its second spatial position; and (2) one or more non-inflation-chamber-control buttons, which are not configured upon depression thereof to cause the increase in pressure in the interior of the inflation chamber, wherein the input module is arranged such that, if suction having a strength of 25 cm $H_2O$ and a flow rate of 4 cc/second is applied to the suction port:

a pressure within the inflatable element is less than 25 cm $H_2O$ at two seconds after completing, and while maintaining, depression of the mechanical inflation-chamber-control button as far as possible toward its second spatial position and without depression of any of the other mechanical user-control buttons of the input module, wherein the input module is arranged such that when the mechanical inflation-chamber-control button is depressed as far as possible toward its second spatial position and without depression of any of the other mechanical user-control buttons of the input module, the flow regulator (a) enables fluid communication between the interior of the inflation chamber and the interior of the inflatable element via the inflatable-element lumen, and (b) enables fluid communication between the suction source (and the interior of the inflatable element via the inflatable-element lumen.

11. The apparatus according to claim 1, wherein the one or more non-inflation-chamber-control buttons comprise a mechanical suction-control button, which is configured to assume at least a first spatial position when not depressed, and a second spatial position when fully depressed, and wherein the input module is arranged such that when the mechanical suction-control button is in its first spatial position, the flow regulator (a) blocks fluid communication between the suction source and the one or more distal suction orifices, and (b) enables fluid communication between the suction source and the interior of the inflatable element via the inflatable-element lumen, and when the mechanical suction-control button is in its second spatial position, the flow regulator blocks fluid communication between the suction source and the interior of the inflatable element.

12. The apparatus according to claim 11, wherein the input module is arranged such that upon depression of the mechanical inflation-chamber-control button as far as possible toward its second spatial position and without depression of the mechanical suction-control button, the flow regulator does not connect the interior of the inflation chamber in fluid communication with the interior of the inflatable element.

13. The apparatus according to claim 11, wherein the input module is arranged such that when the mechanical inflation-chamber-control button is depressed as far as possible toward its second spatial position without depression of the mechanical suction-control button, the flow regulator (a) enables fluid communication between the interior of the inflation chamber and the interior of the inflatable element via the inflatable-element lumen, and (b) enables fluid communication between the suction source and the interior of the inflatable element via the inflatable-element lumen.

14. The apparatus according to claim 11, wherein the mechanical suction-control and inflation-chamber-control buttons are positioned on the input module such that when the mechanical suction-control and inflation-chamber-control buttons are in their respective first spatial positions, the mechanical suction-control and inflation-chamber-control buttons can be depressed and transitioned to their respective second spatial positions by application of a force to the mechanical suction-control and inflation-chamber-control buttons by a single 1 cm-by-2 cm rectangular surface.

15. The apparatus according to claim 14, wherein the input module is arranged such that depression of one of the mechanical suction-control and inflation-chamber-control buttons does not automatically cause depression, by the input module, of the other of the mechanical suction control and inflation-chamber-control buttons.

16. The apparatus according to claim 14, wherein the input module is arranged such that depression of the mechanical suction-control button does not cause an increase in pressure in the interior of the inflation chamber during a transition of the mechanical suction-control button from its first spatial position toward its second spatial position.

17. The apparatus according to claim 14, wherein the input module is arranged such that depression of the mechanical inflation-chamber-control button does not cause connection of the suction source in fluid communication with the one or more distal suction orifices via the suction orifice lumen during a transition of the mechanical inflation-chamber-control button from its first spatial position toward its second spatial position.

18. The apparatus according to claim 14, wherein the input module is arranged such that during simultaneous depression of the mechanical suction-control and inflation-chamber-control buttons, a resulting simultaneous transition of the mechanical suction-control and inflation-chamber control buttons from their respective first spatial positions to their respective second spatial positions causes the flow regulator to:

connect the suction source in fluid communication with the one or more distal suction orifices via the suction-orifice lumen, and connect the interior of the inflation chamber in fluid communication with the interior of the inflatable element via the inflatable-element lumen, thereby inflating the inflatable element, while maintaining the suction source in fluid communication with the one or more distal suction orifices via the suction-orifice lumen.

19. The apparatus according to claim 18, wherein the input module is arranged such that during the simultaneous depression of the mechanical suction-control and inflation-chamber control buttons, the resulting simultaneous transition of the mechanical suction-control and inflation chamber control buttons from their respective first spatial positions to their respective second spatial positions causes the flow regulator:

first, to connect the suction source in fluid communication with the one or more distal suction orifices via the suction-orifice lumen, and thereafter, to connect the interior of the inflation chamber in fluid communication with the interior of the inflatable element via the inflatable-element lumen, thereby inflating the inflatable element, while maintaining the suction source in fluid communication with the one or more distal suction orifices via the suction-orifice lumen.

20. An apparatus for use with a tracheal ventilation tube and a suction source, the apparatus comprising:

(A) a cleaning catheter, which is insertable into the ventilation tube and comprises:

(i) an elongate, flexible, tubular catheter main body, which is shaped so as to define (a) one or more distal suction orifices, (b) a suction-orifice lumen, and (c) an inflatable element lumen: and (ii) an inflatable element, which is mounted to the catheter main body, and which is shaped so as to define an interior that is in fluid communication with the inflatable-element lumen; and (B) an input module, which is coupled to the cleaning catheter, and comprises:

(i) an inflation module, which comprises an inflation chamber separate from the suction source;

(ii) a flow regulator, which is shaped so as to define a suction port coupleable in fluid communication with the suction source; and (iii) a plurality of mechanical user-control buttons, which comprise:

(1) a mechanical inflation-chamber-control button, which is configured to (a) assume at least a first spatial position when not depressed, and a second spatial position when fully depressed, and (b) mechanically and non-electrically cause an increase in pressure in an interior of the inflation chamber during a transition of the mechanical inflation-chamber-control button from its first spatial position toward its second spatial position; and (2) one or more non-inflation-chamber-control buttons, which are not configured upon depression thereof to cause the increase in pressure in the interior of the inflation chamber, wherein the input module is arranged such that upon depression of the mechanical inflation-chamber-control button as far as possible toward its second spatial position and without depression of any of the other mechanical user-control buttons of the input module, the flow regulator does not connect the interior of the inflation chamber in fluid communication with the interior of the inflatable element.

21. An apparatus for use with a tracheal ventilation tube and a suction source, the apparatus comprising:

(A) a cleaning catheter, which is insertable into the ventilation tube and comprises:

(i) an elongate, flexible, tubular catheter main body, which is shaped so as to define (a) one or more distal suction orifices, (b) a suction-orifice lumen, and (c) an inflatable element lumen: and (ii) an inflatable element, which is mounted to the catheter main body, and which is shaped so as to define an interior that is in fluid communication with the inflatable-element lumen; and (B) an input module, which is coupled to the cleaning catheter, and comprises:

(i) an inflation module, which comprises an inflation chamber separate from the suction source;

(ii) a flow regulator, which is shaped so as to define a suction port coupleable in fluid communication with the suction source; and (iii) a plurality of mechanical user-control buttons, which comprise:

(1) a mechanical inflation-chamber-control button, which is configured to (a) assume at least a first spatial position when not depressed, and a second spatial position when fully depressed, and (b) mechanically and non-electrically cause an increase in pressure in an interior of the inflation chamber during a transition of the mechanical inflation-chamber-control button from its first spatial position toward its second spatial position; and (2) one or more non-inflation-chamber-control buttons, which are not configured upon depression thereof to cause the increase in pressure in the interior of the inflation chamber, wherein the input module is arranged such that when the mechanical inflation-chamber-control button is depressed as far as possible toward its second spatial position and without depression of any of the other mechanical user-control buttons of the input module, the flow regulator (a) enables fluid communication between the interior of the inflation chamber and the interior of the inflatable element via the inflatable-element lumen, and (b) enables fluid communication between the suction source and the interior of the inflatable element via the inflatable-element lumen.

* * * * *